US009821116B2

(12) United States Patent
Vouillamoz et al.

(10) Patent No.: US 9,821,116 B2
(45) Date of Patent: Nov. 21, 2017

(54) FLUID DISPENSER

(75) Inventors: Lucien Vouillamoz, Feusisberg (CH); Melissa Rosen, Salem, MA (US); Judy L. Walish, Brighton, MA (US); Daniel Yasevac, Somerville, MA (US); Michel Bruehwiler, Newton, MA (US)

(73) Assignee: Preciflex SA, Biel/Bienne (CH)

( * ) Notice: Subject to any disclaimer, the term of this patent is extended or adjusted under 35 U.S.C. 154(b) by 231 days.

(21) Appl. No.: 14/235,107

(22) PCT Filed: Jul. 25, 2012

(86) PCT No.: PCT/US2012/048044
§ 371 (c)(1),
(2), (4) Date: Jan. 27, 2014

(87) PCT Pub. No.: WO2013/016376
PCT Pub. Date: Jan. 31, 2013

(65) Prior Publication Data
US 2014/0207104 A1 Jul. 24, 2014

Related U.S. Application Data

(60) Provisional application No. 61/576,405, filed on Dec. 16, 2011, provisional application No. 61/511,321, filed on Jul. 25, 2011.

(51) Int. Cl.
*A61M 31/00* (2006.01)
*A61M 5/20* (2006.01)
(Continued)

(52) U.S. Cl.
CPC .......... *A61M 5/20* (2013.01); *A61M 5/14248* (2013.01); *A61M 5/158* (2013.01);
(Continued)

(58) Field of Classification Search
CPC ......... A61M 5/20; A61M 5/158; A61M 5/282
(Continued)

(56) References Cited

U.S. PATENT DOCUMENTS

| 5,050,612 A |   | 9/1991 | Matsumura |
| 5,957,895 A | * | 9/1999 | Sage ................. A61M 5/14248 |
|             |   |        | 604/131 |

(Continued)

FOREIGN PATENT DOCUMENTS

| FR | 1552838 | 1/1969 |
| WO | WO2005/002649 A1 | 1/2005 |

OTHER PUBLICATIONS

International Search Report, International patent application No. PCT/US2012/048044, dated Jan. 31, 2013.
International Search Report, International patent application No. PCT/IB2015/000446, dated Nov. 13, 2015.

*Primary Examiner* — Edelmira Bosques
(74) *Attorney, Agent, or Firm* — Da Vinci Partners LLC; John Moetteli

(57) ABSTRACT

A fluid dispensing device is provided for dispensing a measured amount of fluid into a living organism. The device has a needle having a first end and a second end. The needle is adapted for interfacing, on the first end, with a septum of a flexible hollow membrane, and at a second end thereof, for subcutaneously inserting into a living organism. The needle is guided by a guide to permit an injection into the living organism at a substantially non-orthogonal angle with respect to a surface of the living organism. The first and second ends of the needle pierce their respective piercing surface while translating together in a common direction. In other embodiments, the dispensing device includes a main housing, a flexible fluid reservoir, an injection assembly and a trigger mechanism. The main housing houses the operative components of the device.

8 Claims, 24 Drawing Sheets

(51) Int. Cl.
*A61M 5/158* (2006.01)
*A61M 5/142* (2006.01)
*A61M 5/31* (2006.01)
*A61M 5/32* (2006.01)
*A61M 5/28* (2006.01)

(52) U.S. Cl.
CPC ............ *A61M 5/31* (2013.01); *A61M 5/3286* (2013.01); *A61M 5/2033* (2013.01); *A61M 5/282* (2013.01); *A61M 2005/14252* (2013.01); *A61M 2005/206* (2013.01); *A61M 2005/2073* (2013.01); *A61M 2205/50* (2013.01); *F04C 2270/0421* (2013.01)

(58) Field of Classification Search
USPC ........................................................ 604/506
See application file for complete search history.

(56) References Cited

U.S. PATENT DOCUMENTS

| | | |
|---|---|---|
| 7,896,837 B2 | 3/2011 | Wilkinson et al. |
| 2002/0123740 A1* | 9/2002 | Flaherty ............ A61M 5/14248 604/890.1 |
| 2004/0162521 A1 | 8/2004 | Bengtsson |
| 2006/0095014 A1 | 5/2006 | Ethelfeld |
| 2007/0191780 A1* | 8/2007 | Modi .................... A61M 5/282 604/187 |
| 2009/0088722 A1* | 4/2009 | Wojcik ................ A61M 5/158 604/506 |
| 2009/0254041 A1 | 10/2009 | Krag et al. |
| 2010/0100047 A1 | 4/2010 | Glejbol et al. |
| 2011/0054400 A1 | 3/2011 | Chong et al. |

\* cited by examiner

FLUID DISPENSER

CROSS REFERENCE TO RELATED APPLICATIONS

This application claims the benefit of U.S. Provisional Applications No. 61/511,321, filed Jul. 25, 2011 and No. 61/576,405, filed Dec. 16, 2011, the contents of which are incorporated herein by reference thereto.

COPYRIGHT & LEGAL NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. Further, no reference to third party patents or articles made herein is to be construed as an admission that the present invention is not entitled to antedate such material by virtue of prior invention.

BACKGROUND OF THE INVENTION

This invention relates to fluid dispensers and in particular to fluid dispensers for dispensing a measured amount of liquid in a living organism.

Prior devices that are capable of injecting a fluid in a living organism upon a trigger event are cumbersome and bulky, requiring significant or dedicated space, lack accuracy or only are too costly for many users. For instance, the infusion set described in U.S. Pat. No. 7,879,010 to Hunn et al, the contents of which are incorporated herein by reference thereto, describes a conventional auto-injector in which the needle and injection/retraction mechanism extend perpendicularly from the skin of the patient, thereby creating a bulky and unattractive artificial appendage to the living organism. Further, although Hunn et al describe an adhesive pad, it is not envisioned that such will be adhered to a patient more than the required time to administer the dosage and then removed.

US Publication no 2012/0022499 to Anderson et al, the contents of which are incorporated herein by reference thereto, describes a low-profile device which essentially uses a conventional fluid reservoir, and further has a needle connected to such reservoir via a cannula. Note however the profile height of this device is defined by being at least the length of a needle, given that the needle enters orthogonally to the skin of the living organism being treated.

What is needed is a fluid dispenser that provides an automatic injection of a drug in a living organism upon a trigger event and yet remains simple and highly compact.

What is needed is a fluid dispenser adapted to be left on the living organism many hours, even days, available in the event that such is needed.

What is needed is a fluid dispenser whose profile is not, as a minimum, the depth of penetration of the needle used in the injection.

SUMMARY OF THE INVENTION

A fluid dispensing device is provided for dispensing a measured amount of fluid into a living organism. The device has a needle having a first end and a second end. The needle is adapted for interfacing, on the first end, with a septum of a flexible hollow membrane, and at a second end thereof, for subcutaneously inserting into a living organism. The needle is guided by a guide to permit an injection into the living organism at a substantially non-orthogonal angle with respect to a surface of the living organism. The first and second ends of the needle pierce their respective piercing surface while translating together in a common direction. In other embodiments, the dispensing device includes a main housing, a flexible fluid reservoir, an injection assembly and a trigger mechanism. The main housing houses the operative components of the device. The flexible fluid reservoir is located inside the main housing, and encloses a fluid reservoir. The injection assembly having a needle is in fluid communication with the fluid reservoir. The trigger mechanism triggers the injection assembly to release the needle to inject fluid into the living organism.

The fluid dispensing device is retained (via the user, an elastic band or an adhesive or adhesive pad) against the skin of the living organism and may be manually, automatically or remotely actuated to inject a fluid into the living organism.

An object of the invention is to provide a fluid dispenser which takes up minimal space.

Another object of the invention is to provide a compact fluid dispenser which adapts to requirements which do not readily permit prior art fluid dispensers, such as when such dispenser is worn on a wrist, ankles, a head or around or along some part of human body, or on objects such as clothes and sporting articles.

Those skilled in the art will appreciate that elements in the figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT(S)

The following description is not intended to limit the scope of the invention in any way as they are exemplary in nature and serve to describe the best mode of the invention known to the inventors as of the filing date hereof. Consequently, changes may be made in the arrangement and/or function of any of the elements described in the disclosed exemplary embodiments without departing from the spirit and scope of the invention.

Figure 1:
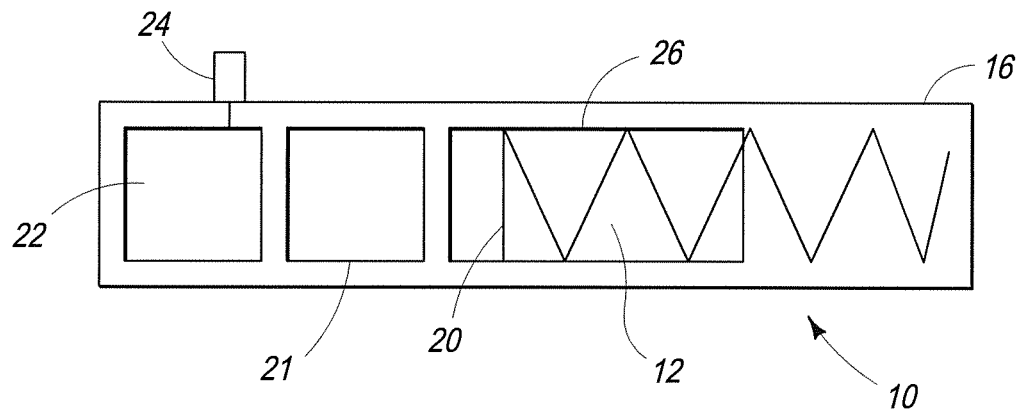
FIG. 1 is a schematic representation of the fluid dispenser of the invention.

Referring now to FIG. 1, in schematic view, the fluid dispenser 10 includes fluid reservoir 26, an optional priming system 21, a trigger mechanism 24, and an injector assembly 22 enclosed in a housing 16.

Figure 2:
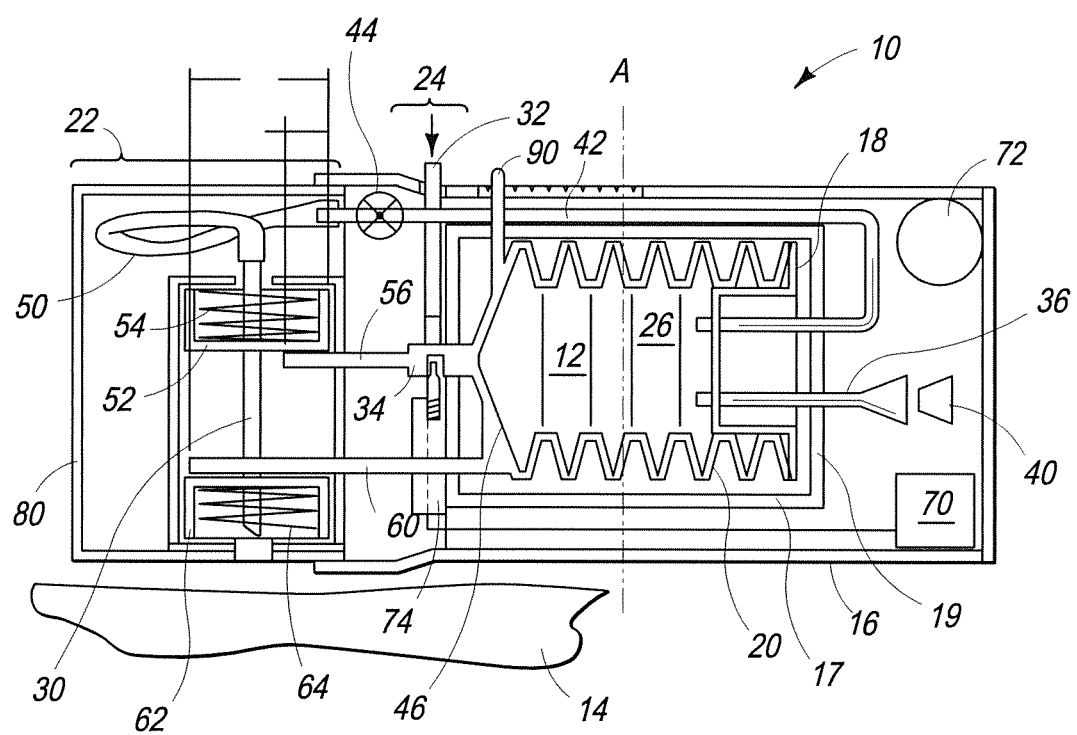
FIG. 2 is a cross sectional side view of the fluid dispenser of the invention.
Figure 3A:
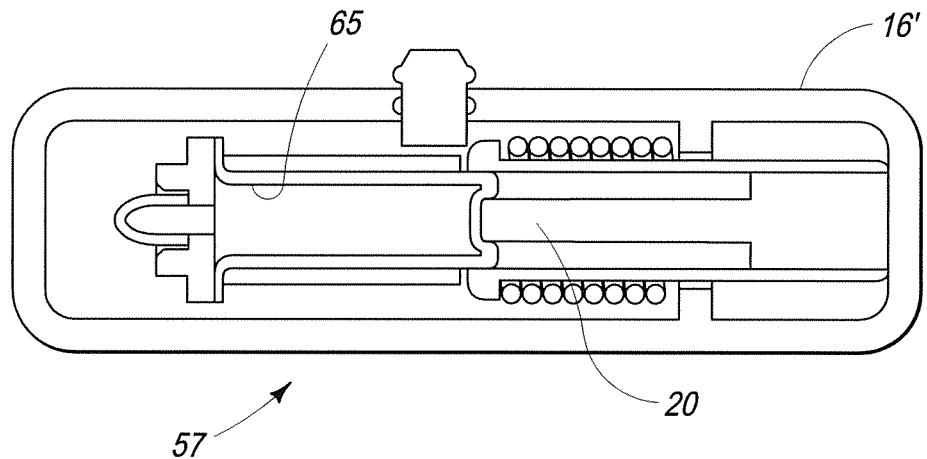
FIG. 3A is a schematic cross sectional view of a second alternate embodiment of the fluid reservoir of the invention, in a first position.
Figure 3B:
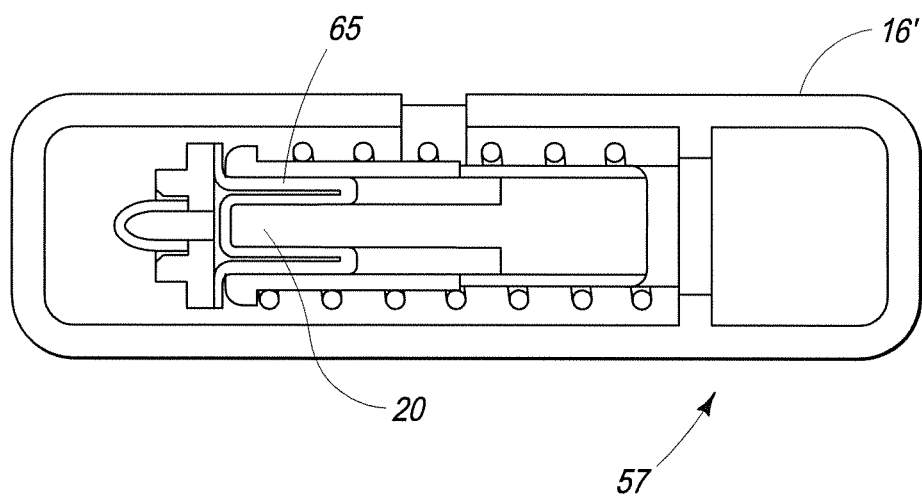
FIG. 3B is a schematic cross sectional view of the second alternate embodiment of FIG. 3A, in a second position.
Figure 4:
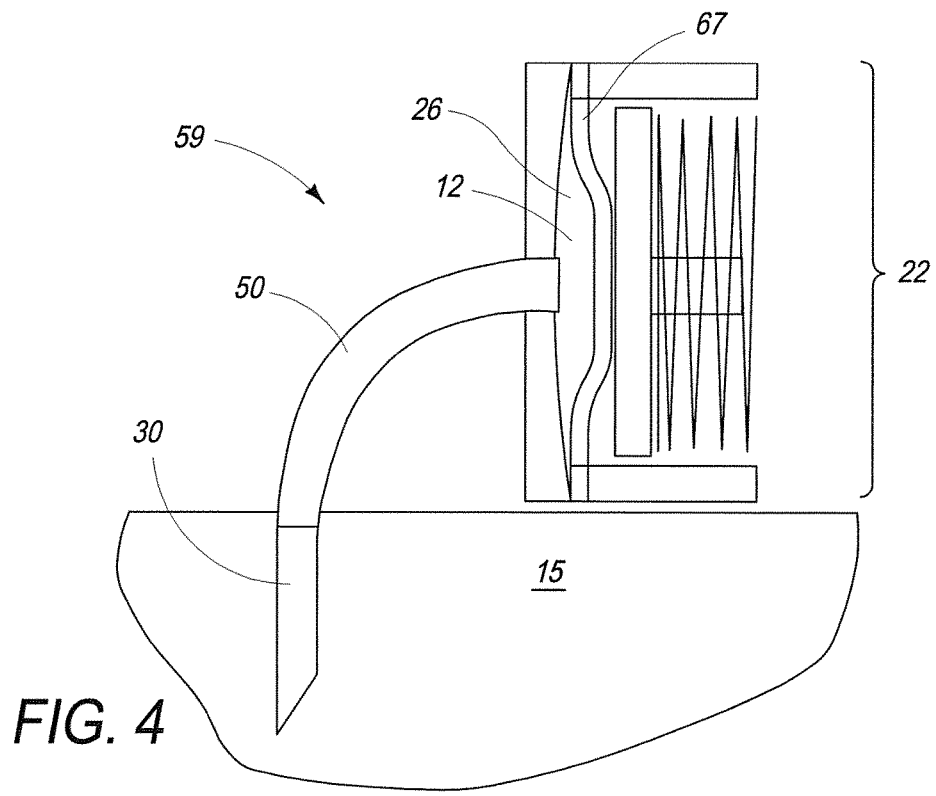
FIG. 4 is a schematic view of a third embodiment of the fluid reservoir of the invention.

Referring now to FIG. 2, a fluid dispensing device 10 of a first embodiment dispenses a measured amount of fluid 12 into a living organism 14. The dispensing device 10 includes a main housing 16, a bellows (or piston device) 20, an injection assembly 22 and a trigger mechanism 24. The main housing 16 houses the operative components of the device 10. The bellows 20 is normally collapsed (opens against an elastic resistance) and is located inside the main housing 16, inside a bellows housing 17 wherein the right side 18 is fixed to a right wall 19 thereof, and further encloses a fluid reservoir 26. Note that, referring to FIGS. 3A, 3B and 4, in alternate embodiments 57 and 59, instead of the bellows 20, a roll-membrane 65 or a flat flexible membrane 67 may be used.

The injection assembly 22 has a needle 30 in fluid communication with the fluid reservoir 26. The trigger mechanism 24 triggers the injection assembly 22 to release the needle 30 to inject fluid 12 into the living organism 14. The trigger mechanism 24 includes a release bar 32, which when depressed, releases a rod 34 which is fixedly attached to the bellows 20 or is an integral part therewith.

In operation, the device 10 must be filled with a fluid 14 for dispensing. The bellows 20 may thus be filled through tube 36, and then sealed using for example a valve or stopper 40 or other closing device. Excess air passes out through the main tube 42 and then a stopper or valve 44 is closed. As the fluid 12 continues to fill the bellows 20, the bellows increases in length, such that the left most side 46 of the bellows moves from the line A to the location shown in the figure. The release bar 32 (shown also in FIG. 5 as bar 10, in various views) is placed so as to lock the left most side 46 of the bellows 20 in position, at which point the valve 44 may be opened. The fluid system remains closed through use of a flexible tube 50 which attaches to the main tube 42. The flexible tube 50 is formed so as to be normally closed and opens only upon receipt of incoming fluid. In this way, the fluid 12 may be sterilely stored in the bellows 20.

The needle 30 of the injection assembly 22 is attached to the flexible tube 50 on one side thereof. The needle 30 includes a cup shaped flange 52 which is integral therewith, which encloses a first extension spring 54. In a set position as shown in the figure, a first motion inhibitor bar 56 extends from the rod 34 so as to block the motion of the needle 30 against downward motion when the bellows 20 is full until the motion inhibitor bar 56 moves far enough to the right to allow the flange 52 to release and to eject the needle 30 into the living organism 14. A second motion inhibitor bar 60 blocks a second cup shaped flange 62 which retains a second extension spring 64. When enough fluid 12 is released into the living organism such that the bellows 20 moves sufficiently to the right to pull the second motion inhibiting bar 60 to free the second flange 62, the second flange 62 abuts the first flange 52 and forces the needle 30 out of the living organism 14. The operation cycle of the device 10 is therefore complete, it having injected the fluid 12 into the living organism 14, followed by automatic retraction of the needle.

The trigger mechanism 24 is controlled by a sensor, a receiver 70, or according to a prescribed dosage, as a function of time. The sensor or receiver 70 may be powered by a power source, such as a battery 72 and control a micro-motor 74 which actuates the actuation bar 32. In this manner, triggering need not be manually initiated.

Optionally, the device 10 further includes a second housing 80 for housing the trigger mechanism 22. The second housing 80 releasably connects to the main housing 16 and may be separately disposable from the main housing and its contents.

The needle 30 of the injection assembly 22 is connected to a flexible catheter 50 which is in fluid communication with the fluid reservoir 26.

The fluid 12 which may be dispensed by the device 10 includes drugs, vitamins suspended in a liquid carrier, anti venoms, serums and medications or hormones such as insulin. The term "drug" used herein includes but is not limited to peptides or proteins (and mimetic thereof), antigens, vaccines, hormones, analgesics, anti-migraine agents, anti-coagulant agents, medications directed to the treatment of diseases and conditions of the central nervous system, narcotic antagonists, immunosuppressants, agents used in the treatment of AIDS, chelating agents, anti-anginal agents, chemotherapy agents, sedatives, anti-neoplastics, prostaglandins, antidiuretic agents and DNA or DNA/RNA molecules to support gene therapy.

Typical drugs include peptides, proteins, hormones including insulin, calcitonin, calcitonin gene regulating protein, atrial natriuretic protein, colony stimulating factor, betaseron, erythropoietin (EPO), interferons such as .alpha., .beta. or .gamma. interferon, somatropin, somatotropin, somastostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues or antagonists thereof, such as IL-1ra; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and analogues thereof; anti-emetic agents such as scopolamine, ondansetron, domperidone, metoclopramide, and analogues thereof; cardiovacular agents, anti-hypertensive agents and vasodilators such as diltiazem, clonidine, nifedipine, verapamil, isosorbide-5-monotritate, organic nitrates, agents used in treatment of heart disorders, and analogues thereof; sedatives such as benzodiazepines, phenothiazines, and analogues thereof; chelating agents such as defroxanune, and analogues thereof; anti-diuretic agents such as desmopressin, vasopressin, and analogues thereof; anti-anginal agents such as fluorouracil, bleomycin, and analogues thereof; anti-neoplastics such as fluorouracil, bleomycin, and analogues thereof; prostaglandins and analogues thereof; and chemotherapy agents such as vincristine, and analogues thereof, treatments for attention deficit disorder, methylphenidate, fluvoxamine, bisoprolol, tacrolimus, sacrolimus, cyclosporine, Actemra (tocilizumab), Adcretris (brentuximab vedotin), Arzerra (ofatumumab), Avastin (bevacizumab), Benlysta (belimumab), Cimzia (certolizumab pegol), Erbitux (cetuximab), Herceptin (trastuzumab), Humira (adalimumab), Ilaris (canakinumab), Lucentis (ranibizumab), Mylotarg (gemtuzumab ozogamicin), Perjeta (pertuzumab), Prolia (denosumab), Remicade (infliximab), Simponi (golimumab), Soliris (eculizumab), Stelara (ustekinumab), Tysabri (natalizumab), Vectibix (panitumumab), Xgeva (denosumab), Xolair (omalizumab), Yervoy (ipilimumab), and Zevalin (ibritumomab tiuxetan).

Optionally, the device 10 may include an indicator 90 which extends outside the housing 16 through an axially elongated slot having demarcations along its length, so as to enable the indicator 90 to indicate an amount of such fluid 12 administered to the living organism 14.

In an alternate embodiment, the power supply 22 can be solar cells, a wound watch spring, movement captured by an oscillating mass (such as used in automatic watches), or a pneumatic system storing compressed air.

A suitable motor 74 is referred to by its trademark SQUIGGLE™, available from New Scale Technologies, Inc. of New York, USA.

Figure 11A:
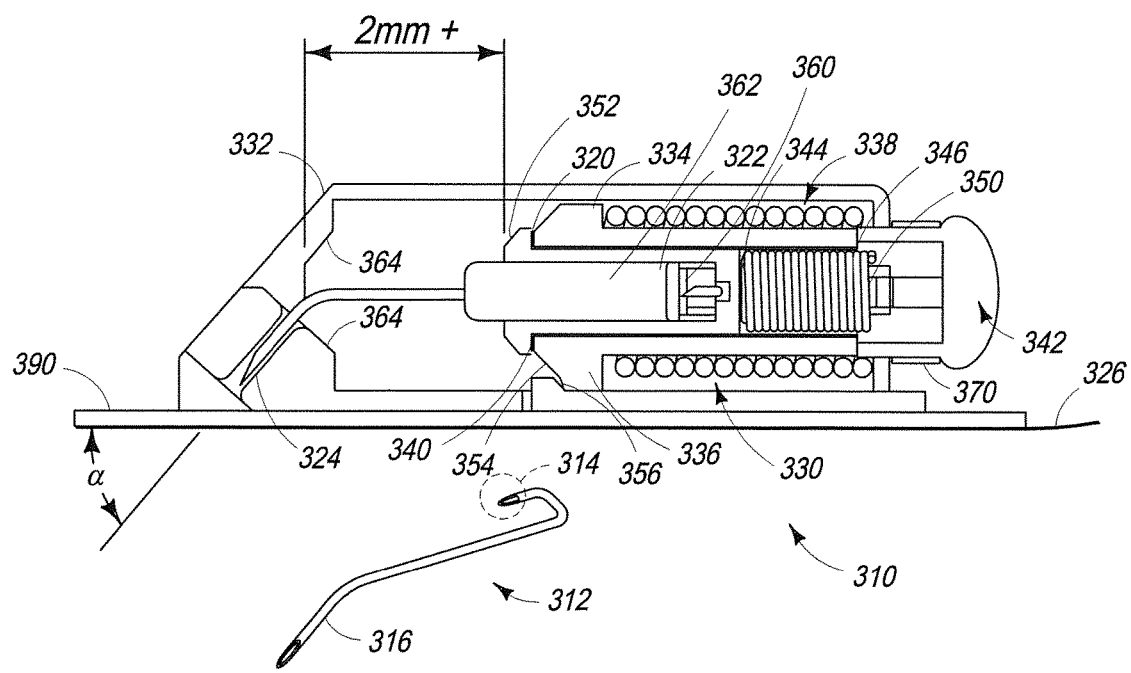
FIG. 11A is a cross-sectional view of a fifth alternate embodiment of the invention.
Figure 11B:
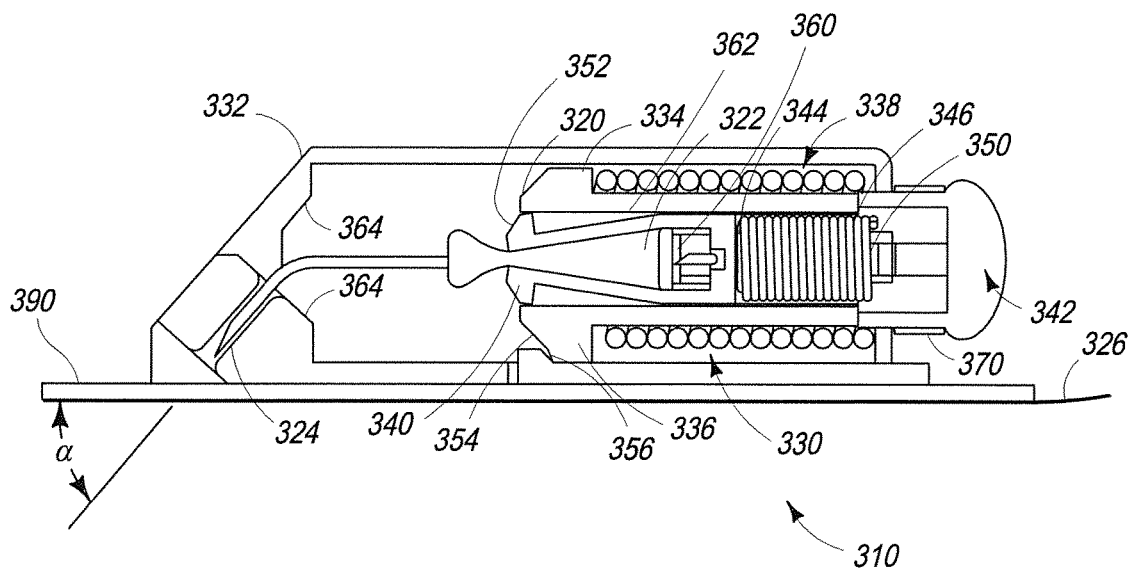
FIG. 11B and FIG. 11C are progressive, partial cross section views of the fifth alternate embodiment of FIG. 11A, showing the progress of the needle during an injection cycle.
Figure 11C:
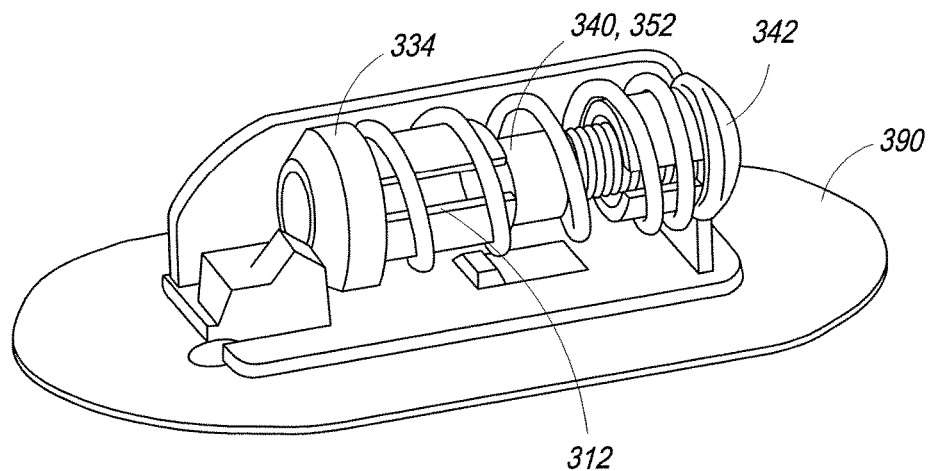
Figure 11D:
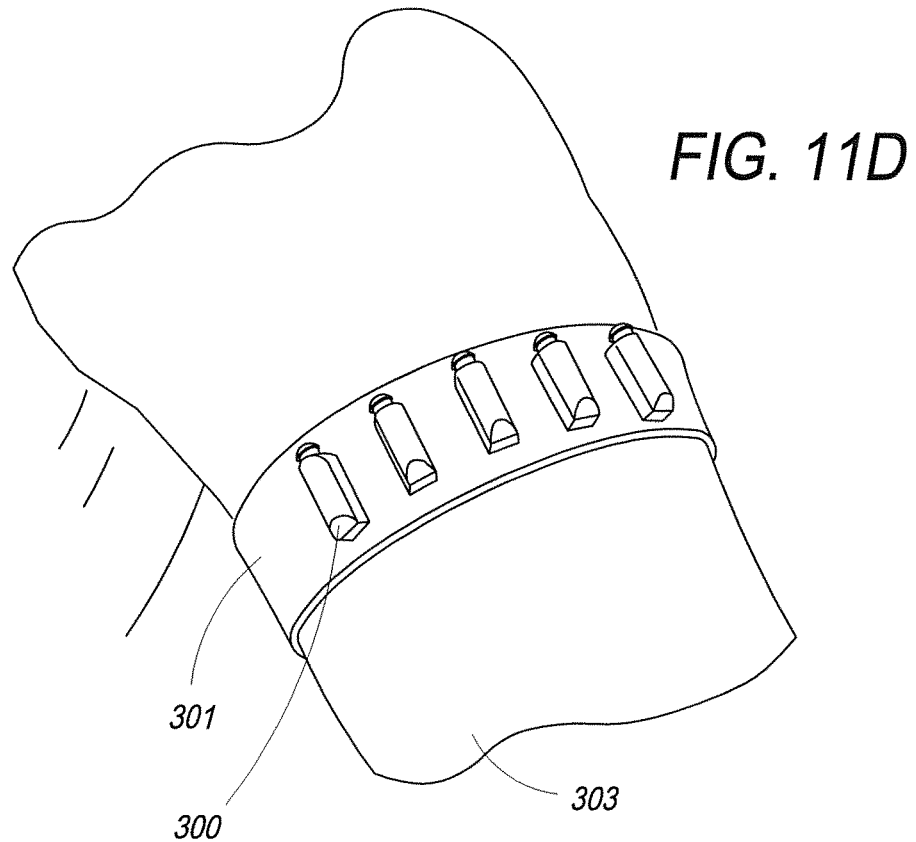
FIG. 11D is a perspective view of a holder for the fifth alternate embodiment of FIG. 11A.
Figure 11E:
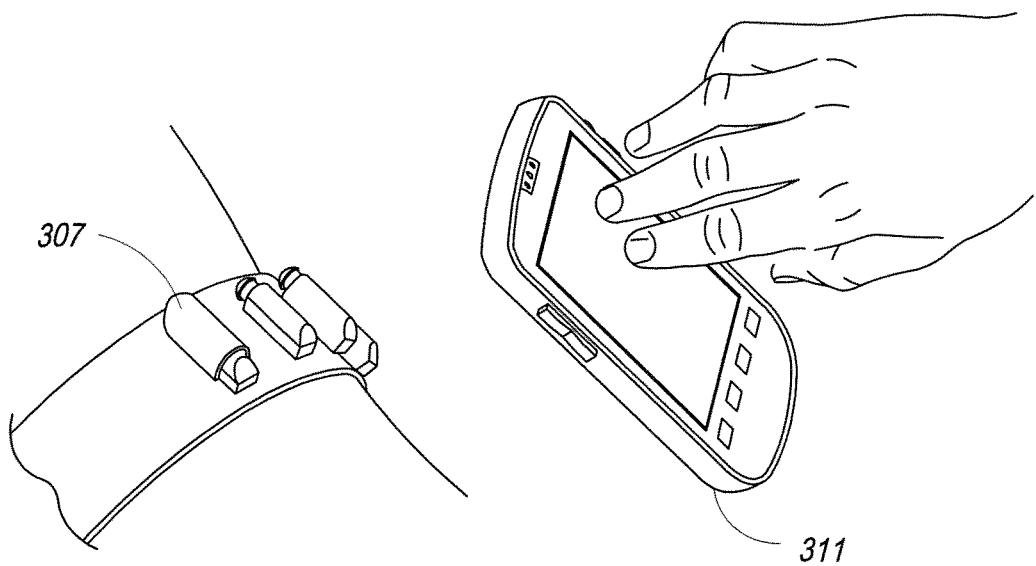
FIG. 11E is a perspective view of a remote actuation device for use with the invention.

In an alternate embodiment, the device 10 is held against the skin 15 of the living organism 14 by a band (see for example FIG. 11D) such as a watch band.

In an embodiment, the device 10 uses a micro bellows 20 such as those available from Servometer/PMG LLC of Cedar Grove, N.J., USA (PN 400-31988).

Figure 5:
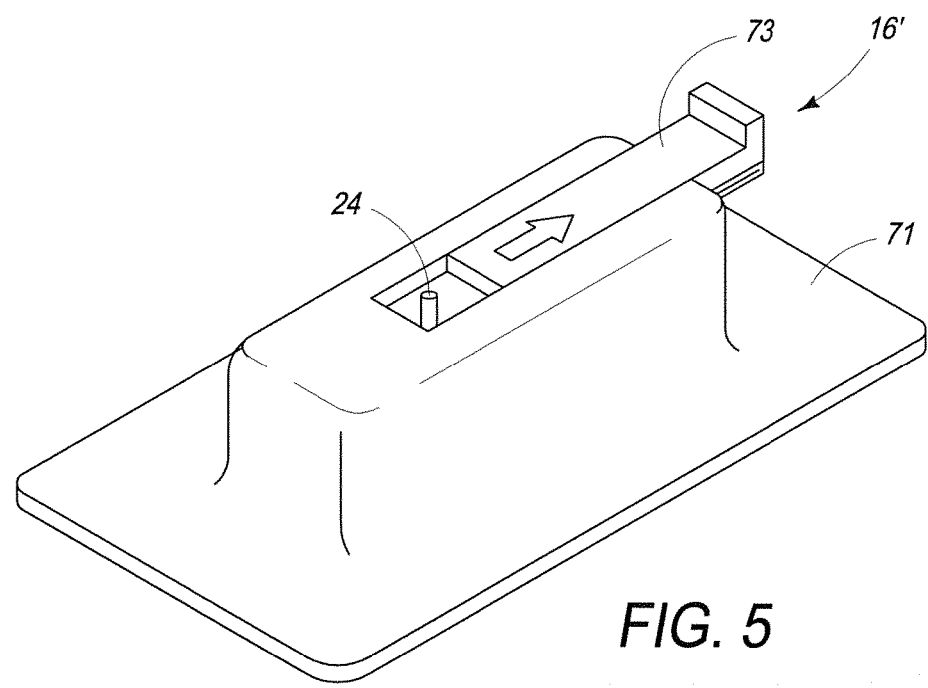
FIG. 5 is a perspective view of an enclosure for the fluid dispenser of the invention.
Figure 6:
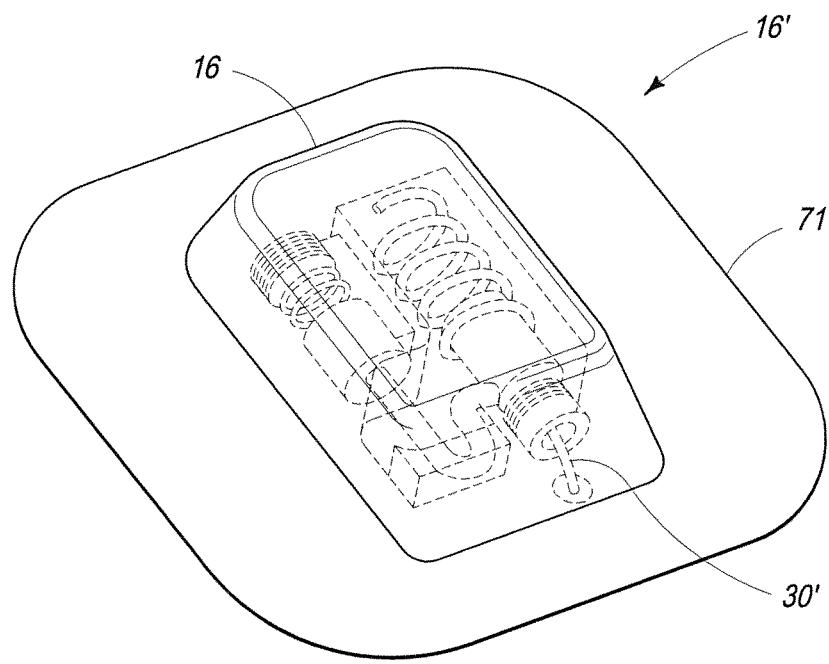
FIG. 6 is a perspective view of a second enclosure for the fluid dispenser of the invention.
Figure 7:
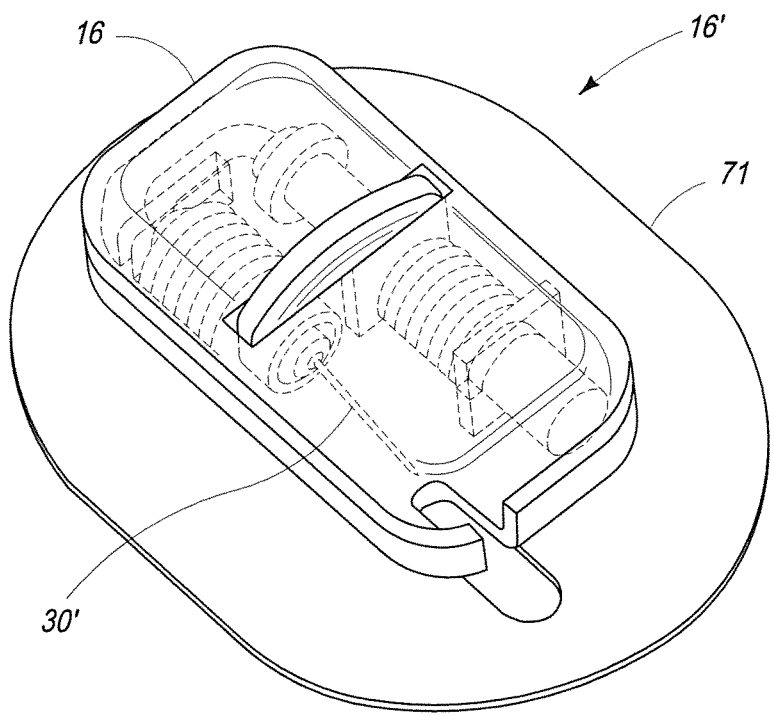
FIG. 7 is a perspective view of a third enclosure for the fluid dispenser of the invention.

The micro injector deals with a volume of 15 μL to 30 μL and subcutaneously (>5 mm) injects a fluid within a time frame of 0.5 to 2 sec. A suitable needle size is between 0.3 to 0.45 mm. Preferably, the overall size of the packaging 16' shown in FIG. 5 is about 4 mm in diameter and about 15 mm long. Referring now to FIG. 6, the packaging 16' is fixed by gluing on or adhering to the skin with auto-adhesive sticker portion 71. Note that the adhesive should be selected so that, after wearing of the fluid injector, the adhesive may be cleaned away with alcohol, enabling the injector to be re-attached in the event that use during a first wearing of the injector was not necessary. The packaging 16' is comprised of a housing 16 and a closure 73 such as a sliding panel to prevent access to the trigger 24 until a fluid is to be dispensed. Optionally, a septum of a thin, elastic material (not shown, as it's on the underside of the device between the needle and the skin of the user) seals the needle injector mechanism 22 from external elements. Note that the sliding panel 73 can be replaced by a remote trigger such as an RF trigger or timed trigger device shown in FIG. 10. A further security device (not shown) which prevents against accidental triggering may be added to improve safety or which is resistant to vibration or shock or material creep.

Figure 8:
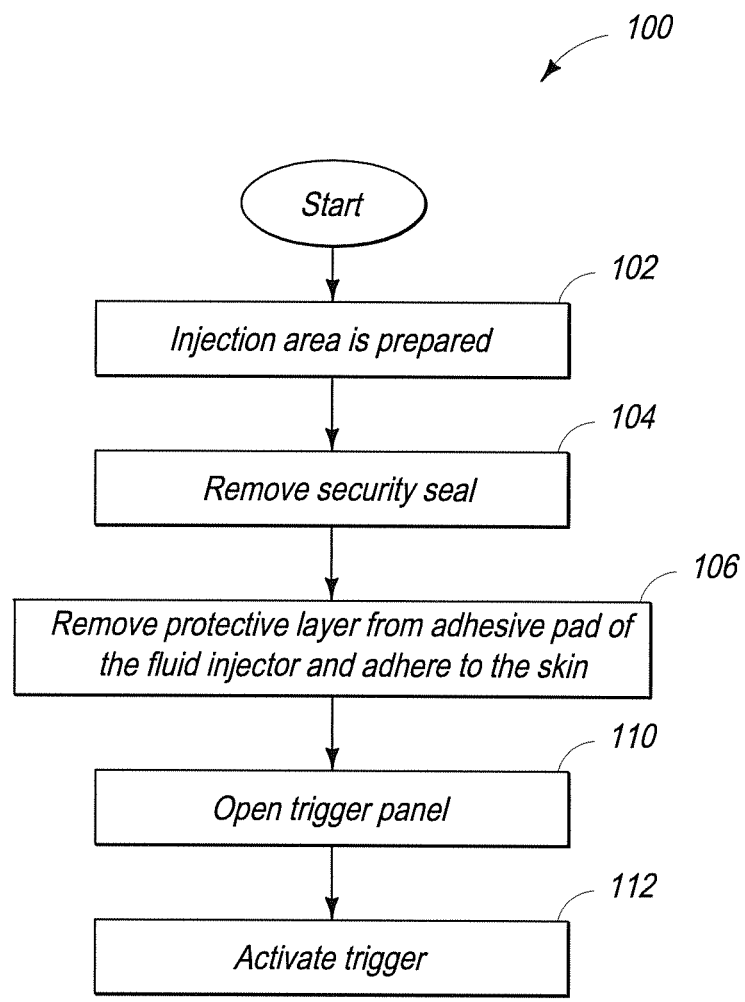
FIG. 8 is a flow chart of an initialization method of the invention, performed by a user or medical professional.

Referring to FIG. 8, a method 100 of using the invention includes several steps. In a first step 102, the injection area is prepared, for example, cleaning with a disinfectant and a cotton swab. In a second step 104, a security seal on the fluid injector is removed by the user. In a third step 106, a protective layer is removed from an adhesive pad of the fluid injector and the fluid injector is adhered to the skin of the user. In a fourth step 110, the trigger panel is opened by the user to allow access to the trigger. In a fifth step 112, the trigger is activated by the user, thereby initiating the automated process of fluid injection.

Figure 9:
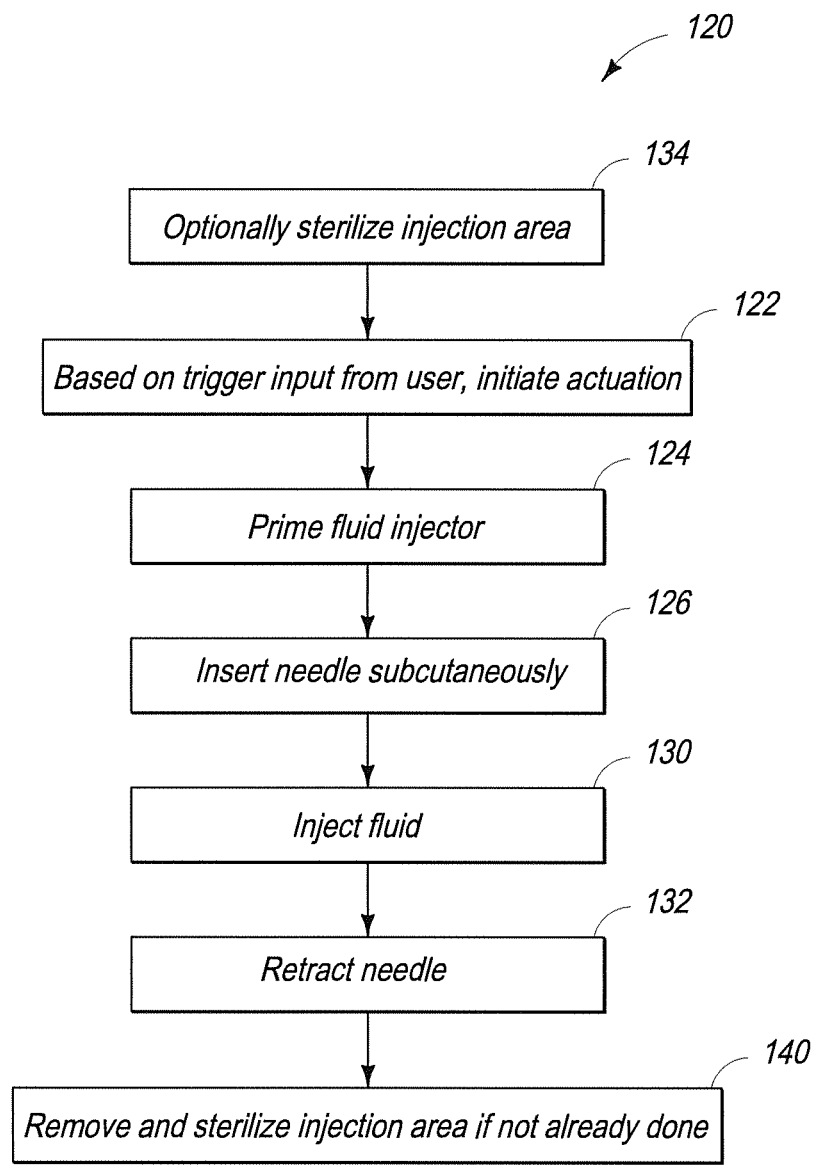
FIG. 9 is a flow chart of a method of the invention executed by the fluid injector.

Referring to FIG. 9, the automated process 120 of fluid injection is executed by control electronics in the fluid injector and includes several steps. In a first automated step 122, the actuation system of the invention is initiated. In a second automated step 124, the fluid injector is primed. In a third automated step 126, the needle is inserted subcutaneously. In a fourth automated step 130, the fluid is injected. In a fifth automated step 132, the needle is retracted. After use, the fluid injector 140 may be removed by the user and the injection area sterilized, if this has not already been performed.

Figure 10:
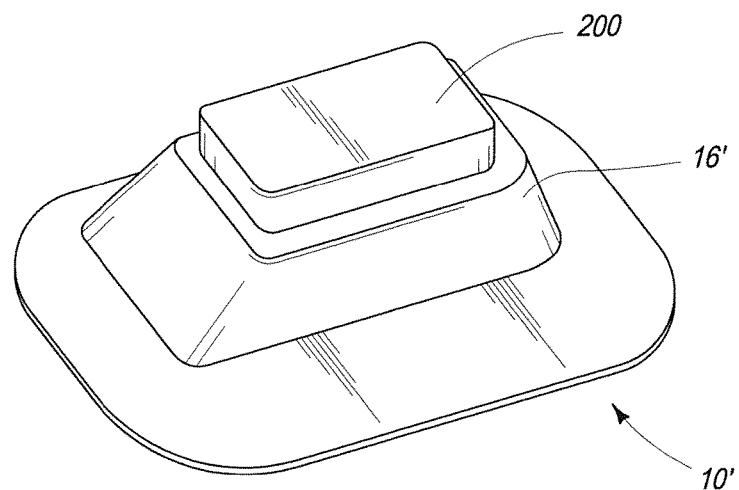
FIG. 10 is a perspective view of a fourth alternate embodiment of the invention, with a modular, remote triggering device of the invention.

Referring to FIG. 10, the trigger mechanism 24 can be controlled via wireless interface in a control module 200 that may be clipped on to the fluid injector 10' so as to interface with the trigger in a manner which can actuate the trigger.

Referring now to FIGS. 11A to 15, in other embodiments 300, 400, 500, 600, and 700, the fluid reservoir 12 is a flexible fluid reservoir. The flexible fluid reservoir is located inside the main housing. The injection assembly having a needle is in fluid communication with the fluid reservoir. The trigger mechanism triggers the injection assembly to release the needle to inject fluid into the living organism.

Referring in particular to FIGS. 11A to 11E, a fluid dispensing device 310 of an alternate embodiment has a needle 312 having a first end 314 and a second end 316, preferably beveled to facilitate piercing of the skin of the living organism. The needle 312 is adapted for interfacing, on the first end 314, with a septum 360 in a wall 320 of a flexible hollow membrane 322, and at the second end 316 thereof, for subcutaneously inserting into a living organism. The needle 312, about its second end 316, is guided by a guide 324 to permit an injection into the living organism at a substantially non-orthogonal angle alpha with respect to a surface 326 of the living organism. An injection mechanism 330 within a housing 332 includes a hollow transfer collet 334 having a flange 336 at one end thereof and arranged to be translatable lengthwise therein, an extension spring 338 into which the collet 334 is disposed, the extension spring 338 bearing against the flange 336 at one end thereof and against the housing 332 at the other end thereof, a flexible membrane receiver 340 which is disposed within the transfer collet 334, the flexible membrane receiver 340 having a the needle 312 affixed therein such that the first end 314 is held adjacent the flexible membrane 322 (preferably having a 20 µl capacity) when installed in the receiver 340 and such that the second end 316 is received into the guide 324, and a user push button 342 which abuts one end of the collet 334 and extends outside the housing 332 so as to be accessible by a user. The flexible membrane receiver 340 is connected to a first end 344 of a compression spring 346 having a lesser spring constant K as compared to the extension spring 338, the spring 346 being connected at an opposite end 350 to the housing 332. The flexible membrane receiver 340 having a flange 352 at one end thereof that extends beyond an end face 354 of the flange 336 of the collet 334. In the view shown in FIG. 11A, the extension spring 346 is in an essentially relaxed state and the compression spring 338 is in a stressed state. A retaining shoulder 356 on a tang in the housing 332 maintains the compression spring 338 in the stressed state.

In operation, a user pushes the button 342 which reacts against the collet 334 to bias the collet over the retaining shoulder 356, thus allowing the compression spring 338 to expand, thereby translating the flexible reservoir 322 in the receiver 340 along with the needle 312 to an opposite end of the housing 322. During this translation, the first end 314 of the needle 312 penetrates a septum 360 of the fluid reservoir 322 and is primed with the fluid 362 contained therein as the needle 312 is guided by the guide 324 toward the surface 326 of the living organism. Further translation, optionally, after priming, then plunges the needle 312 into the living organism 14 a prescribed depth, usually 3 to 5 mm. The receiver flange 352 is sloped so that when it reaches a matched slope or cam surface 364 formed on an inner surface of the housing 332, the receiver 340, which is slotted, collapses (see FIG. 11C) to further squeeze the fluid 362 out of the reservoir 322, expelling the remaining amount of such fluid. In this way, the squeezing is performed laterally with respect to an axis along which the trigger mechanism is actuated. As the receiver flange 352 collapses, the receiver is able to pass through the collet 334, drawn therethrough by the extension spring 338 and thus simultaneously drawing the needle 312 out of the living organism 14 safely into the housing 322. Note that here, aspiration of fluids from the body of the living organism is prevented due to the fact that pressure is maintained on the membrane by the tangs of the receiver 340 being held in a collapsed position by the inner surface of the collet 334. At this point, the fluid dispensing device 310 may be removed from the surface 326 of the living organism 14 and be discarded.

As a security against inadvertent activation, a locking construct 370 prevents the push buttons 342 from being depressed.

Referring now to FIG. 11G, the fluid dispensing device 300 is retained (via the user holding it against the skin using hand pressure, or via an elastic band 301 or an adhesive or adhesive pad) against the skin of the living organism 14 and may be manually, automatically or remotely actuated to inject a fluid into the living organism 14. For example, the user may simply hold the device 300 against the skin of the living organism 14 to be treated. Alternatively, the elastic band 301 on which the dispensing device 300 (or a series thereof as shown) is affixed may be extended and fastened around an appendage 303 of the living organism 14 so that the base of the housing 332 through which the needle 312 passes is held securely against the skin. For example, the device 300 may be contained in a watch casing mounted on a watch bracelet, such as shown in PCT Application No. PCT/IB2010/002055 and PCT/IB2010/002054, the contents of which are incorporated herein by reference thereto. Optionally, according to the tastes of the wearer, the bracelet and casing may be decoratively formed and/or made of precious metals. Still further, the housing 332 may include a base having a surface on which an adhesive may be applied prior to affixing the device against the skin of the living organism. A self-adhesive pad 390, 490, 590 (e.g. such as that shown in FIGS. 12A and 13A) may also be used.

Referring now to FIG. 11H, the device 300 may include an attachment 307 into which the device 300 may be placed, the attachment 307 including a radio receiver or the like and an actuator, which receives command signals from a mobile device 311 to actuate the actuator at given times, to automatically administer a dose of fluid to the living organism 14.

Figure 12A:
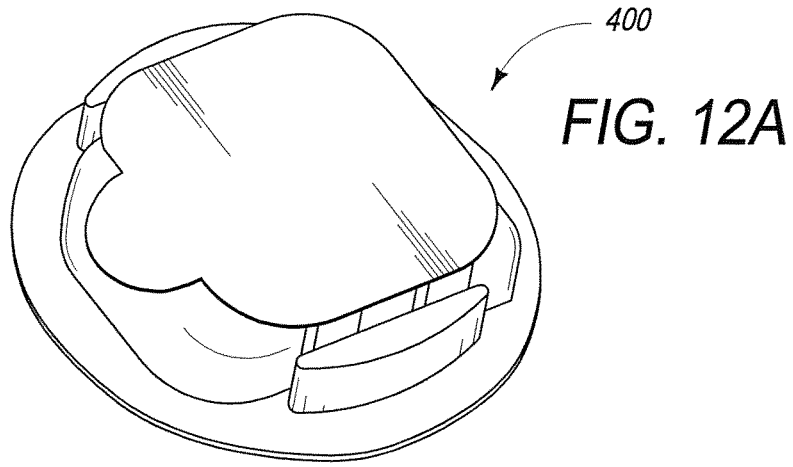
FIG. 12A is a perspective view of a sixth alternate embodiment of the invention.
Figure 12B:
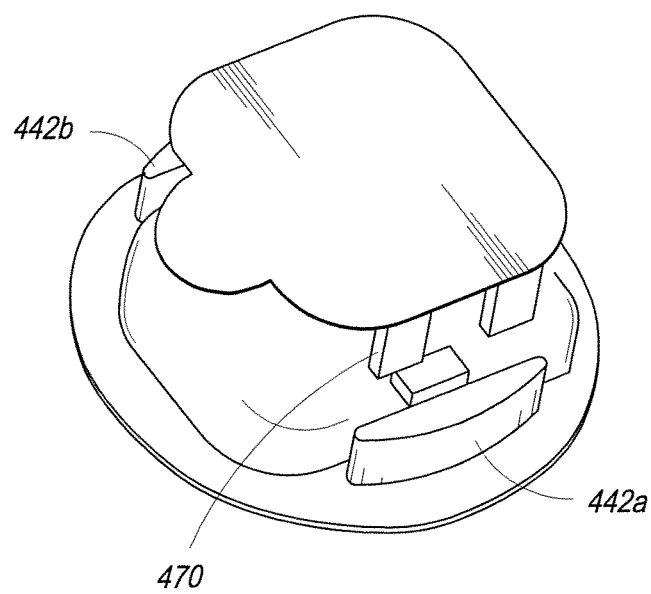
FIG. 12B is a second perspective view of the sixth alternate embodiment of the invention, showing removal of a safety lock.
Figure 12C:
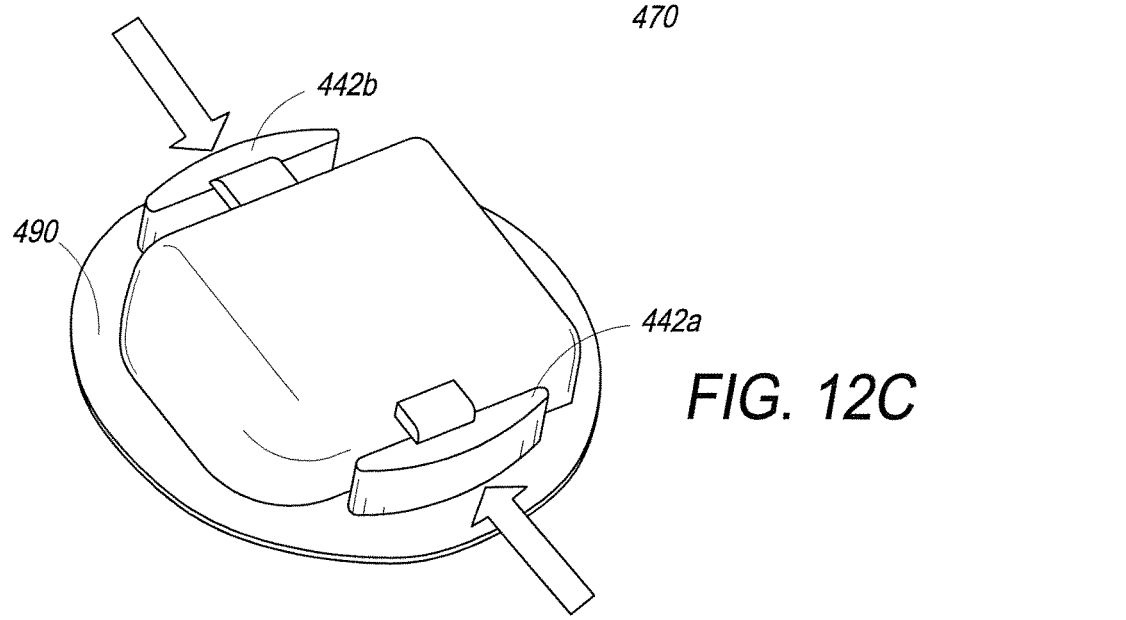
FIG. 12C is a third perspective view of the sixth alternate embodiment of the invention, showing actuation of the device.
Figure 12D:
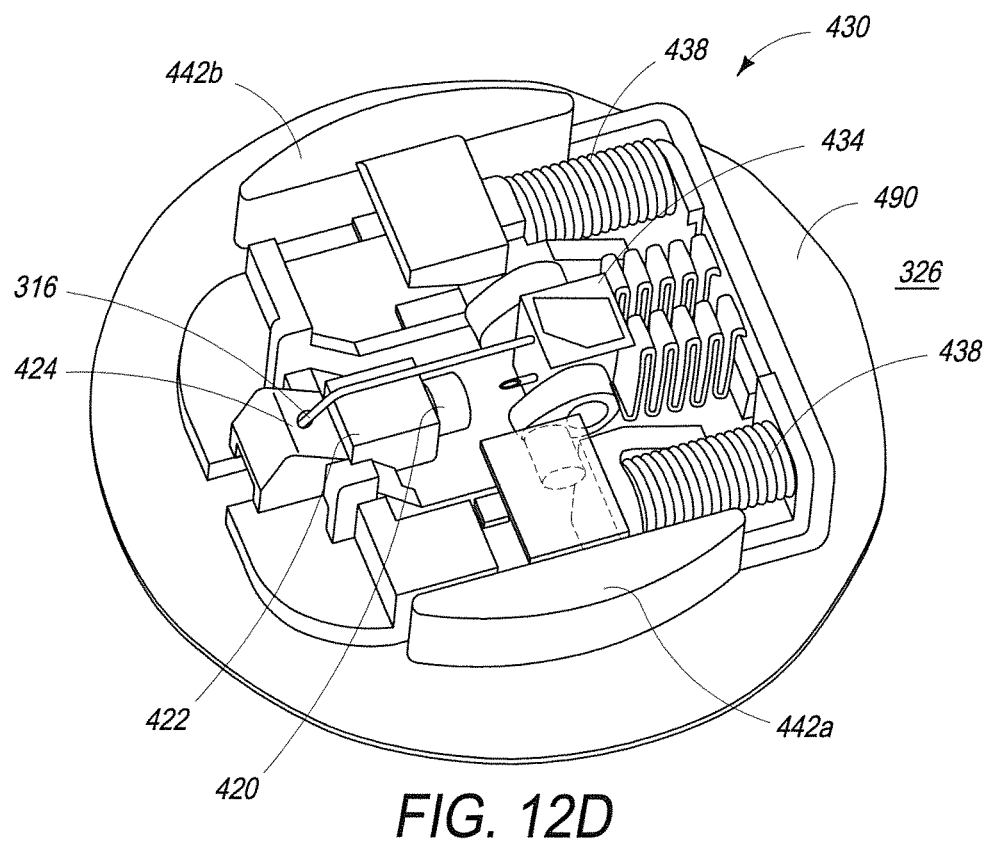
FIG. 12D is a cut-away view of the sixth alternate embodiment of the invention, just prior to actuation.
Figure 12E:
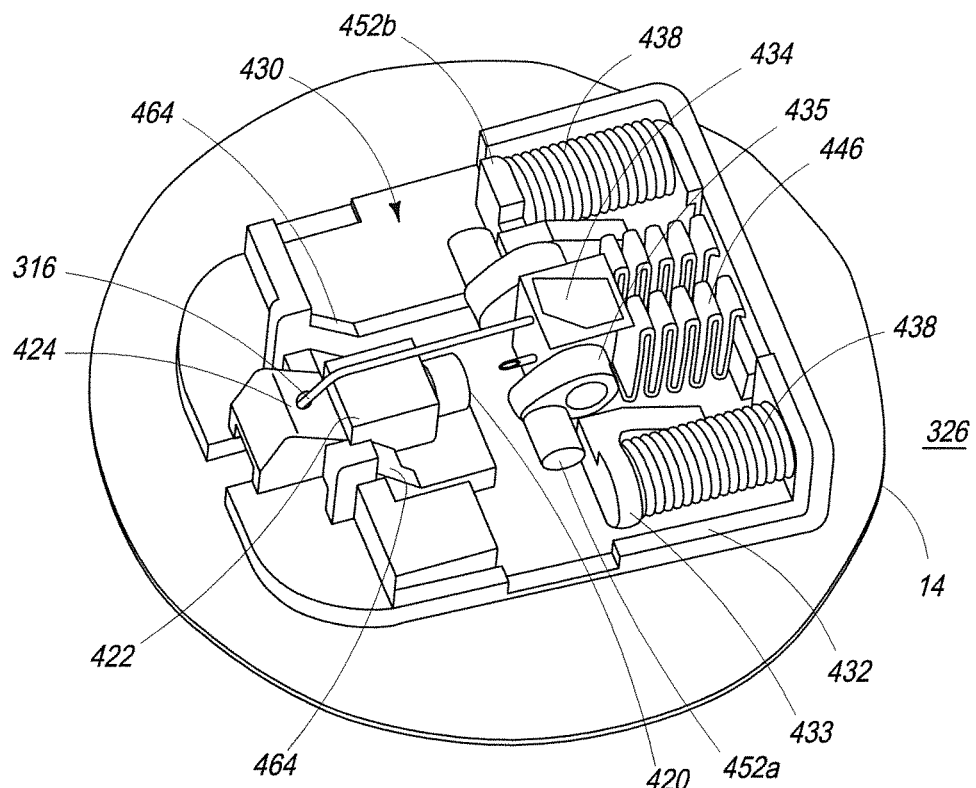
FIG. 12E is the cut-away view of FIG. 12D, but with the push button structure shown with hidden lines.
Figure 12F:
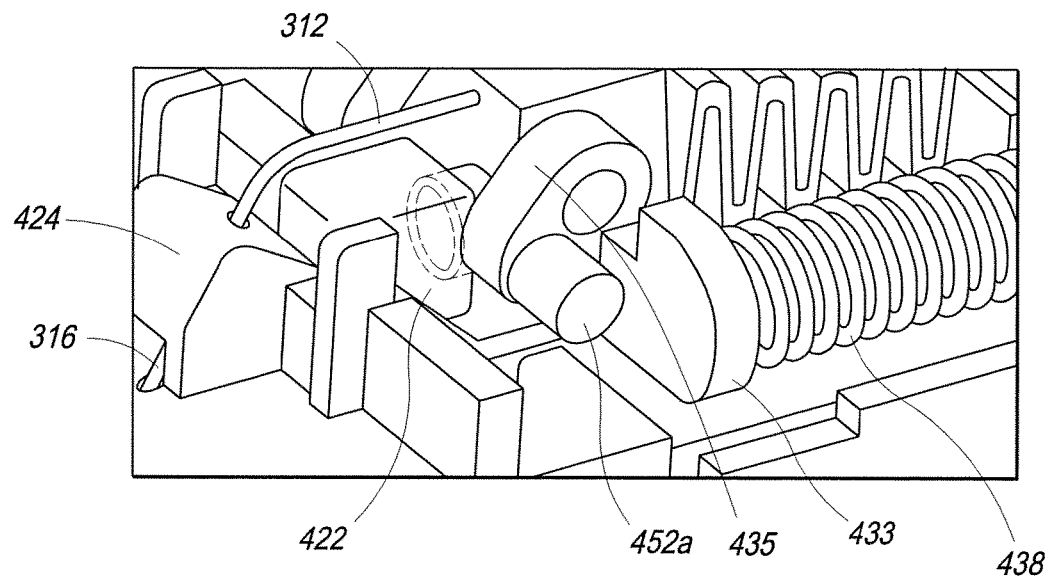
FIG. 12F is a close-up, cut-away view of the sixth alternate embodiment of the invention.
Figure 12G:
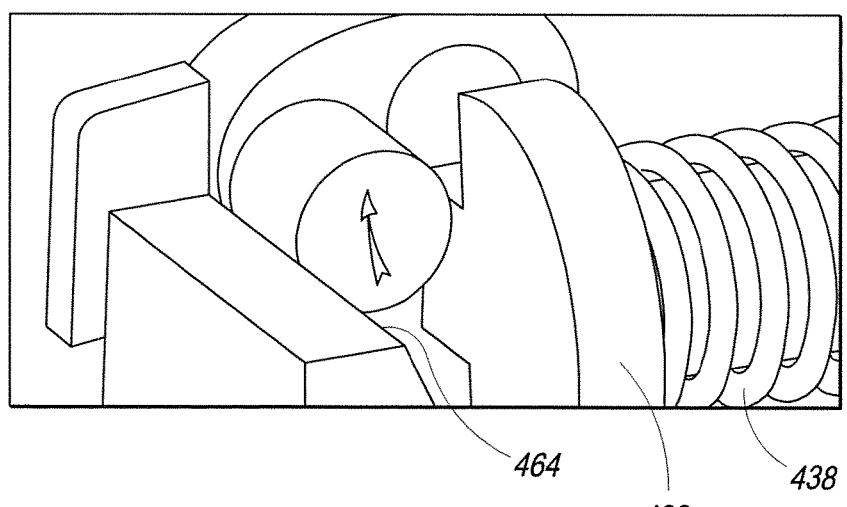
FIG. 12G is a further close-up, cutaway view of the sixth alternate embodiment of the invention, showing further motion in the mechanism.
Figure 13A:
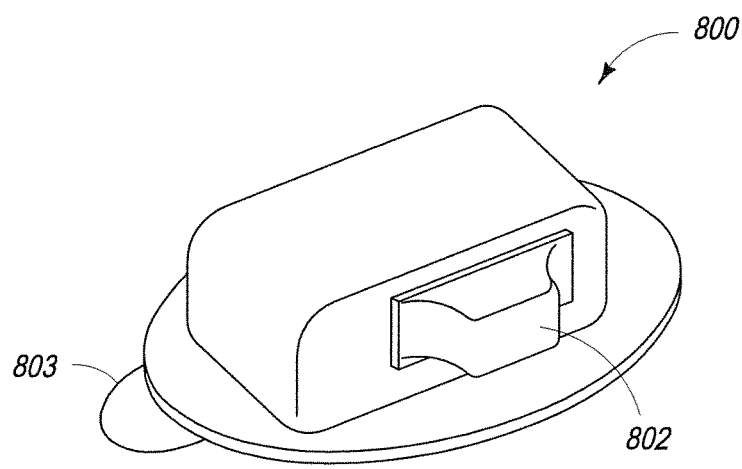
FIG. 13A is a perspective view of a seventh embodiment of the invention.
Figure 13B:
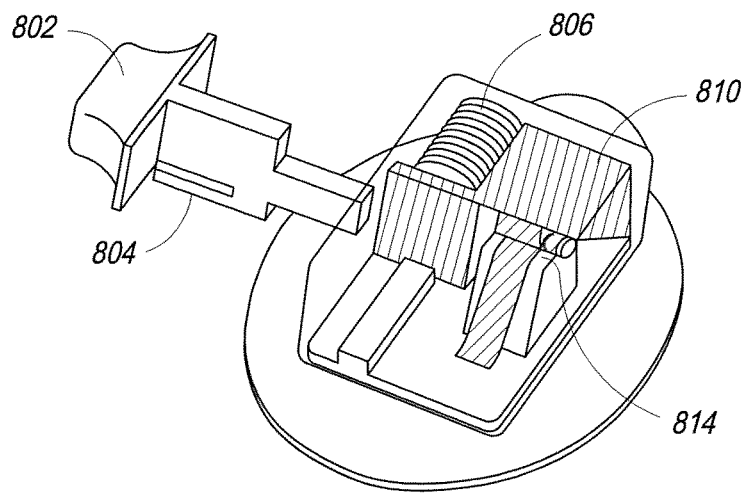
FIG. 13B is a perspective, partially transparent view of the seventh embodiment of the invention.
Figure 13C:
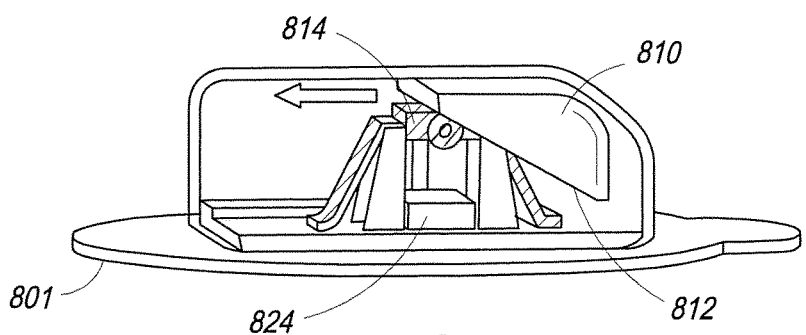
FIG. 13C is a perspective, partially transparent view of the seventh embodiment of the invention.
Figures 13D, 13E:
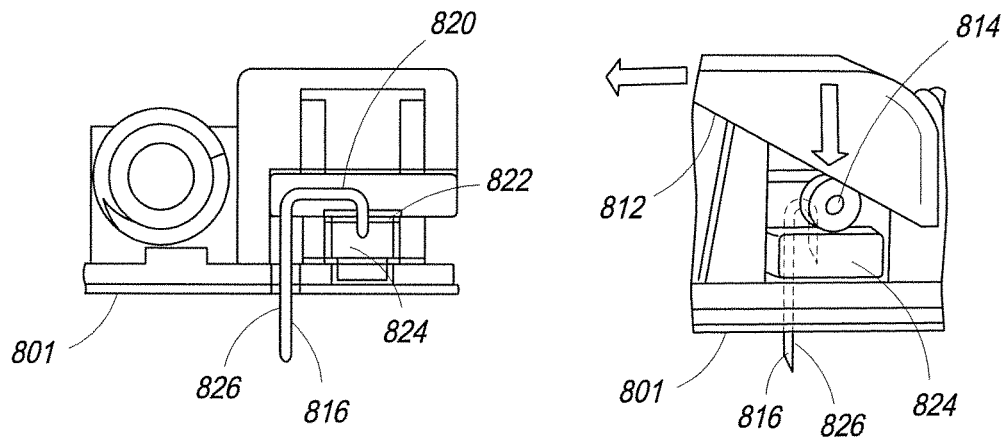
FIG. 13D is a cross sectional view of the seventh embodiment of the invention.
FIG. 13E is a partial perspective view of the seventh embodiment of the invention.
Figure 13F:
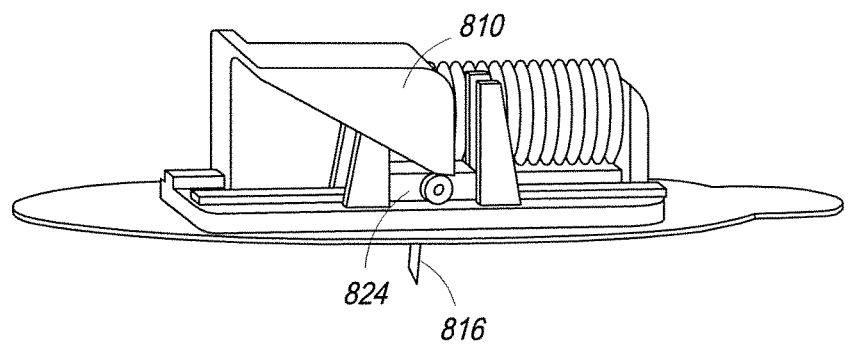
FIG. 13F is a perspective view of the seventh embodiment of the invention.
Figure 13G:
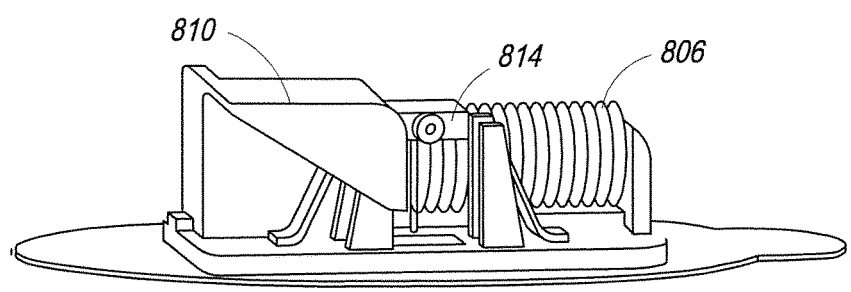
FIG. 13G is a perspective view of the seventh embodiment of the invention.

Referring to FIG. 12A to FIG. 12G, an alternate fluid dispensing device 400 has a needle 312 having a first end 314 and a second end 316. Referring in particular to FIGS. 12D and 12E, the needle 312 is adapted for interfacing, on the first end 314, with a septum 420 of a flexible hollow membrane 422, and at the second end 316 thereof, for subcutaneously inserting into a living organism 14. The needle 312, about its second end 316, is guided by a guide 424 to permit an injection into the living organism 14 at a substantially non-orthogonal angle alpha with respect to a surface 326 of the living organism.

Injection at a non-orthogonal angle helps ensure that the device has a low profile with respect to the surface of the living organism to be injected. As can be appreciated, if one must inject to a depth of 5 mm to be sure to inject into the subcutaneous layer of the skin, than using a conventional injection system, the system must extend orthogonally above the surface to be injected at the very least, 5 mm as well. By entering the skin at an angle, and by using a needle which is ductile or malleable in that it can be deformed through a guide (see for example FIG. 20B), it is possible to use a long mechanism without having an excessively high or proud profile. Having a low profile has the advantage of making it more difficult for a wearer to inadvertently tear away the device during a period of prolonged use as well as makes the device more invisible while it is worn. Further, there is an aesthetic aspect when used on humans: objects foreign to the human body, attached directly to the body are best unseen or invisible. An infusion device attached to the body is considered by many to be unattractive, much like a wart. Consequently, it is important that the device of the invention be as small and low profile as possible.

An injection mechanism 430 within the housing 432 includes a transfer block 434 arranged to be translatable lengthwise therein, compression springs 438 (fixed at one end to the housing 432 and at another to a spring slide 433) which bias the block 434 to translate toward an opposite end of the housing 432. The needle 312 is affixed in the block 434 such that, when the block is released to translate to the opposite end of the housing 432, it lodges in the septum 420. User push buttons 442a and 442b (shown most clearly in FIG. 12D) slide laterally in the housing 432, and when they are in the un-depressed position as shown, they prevent the block 434 from translating against the flexible reservoir 422 by locking the compression springs 438 in a stressed position. When the push buttons 442a and 442b are depressed inwardly, they release the compression springs 438 which have a high spring constant K (typically 10 times higher than return extension spring 446), to translate the block 434 via a cam 435 to the opposite end of the housing 432. The block 434 then is depressed by spring action against the reservoir 422, squeezing the reservoir and thus forcing the fluid therein to prime the needle 312 and plunging the second end 316 of the needle 312 into the living organism 14. Once the fluid in the reservoir 422 is depleted, arms 452a and 452b of the cam 435 (which pivot on the block 434) ride up a corresponding cam surface 464 to clear the spring slide 433 and compression springs 438, thus freeing an extension spring 446 which is fixed at one end to the block and at an opposite end, to the housing 432, to draw the block 434 together with the needle 312, to return the block and thus remove the needle from the living organism 14, retracting it safely into the housing 432.

Referring in particular to FIG. 12B, as a security against inadvertent activation, a locking construct 470 prevents the push buttons 442a and 442b from being depressed. Alternately, a film retainer strap around the springs and affixed (e.g., bonded) to the housing may be used to lock the structure, the film being made of a material which may be selectively melted by applying a resistance or magnetic induction to an attached metal strip. The heated strip melts the retainer strap releasing the device to perform an injection and retraction. Materials with a low melting point, such as polypropylene or Tyvek may be used. A metal component, made, for example, of titanium or other conductor that changes temperature in response to current, may be used. The metal component is in contact with the film. The metal may be titanium, for example, or other conductor that changes temperature in response to current. An external device applies current to metal component by direct contact or via magnetic induction. The metal rod heats and applies local heat to the film, melting a portion thereof so as to initiate a tear and breakage, thereby releasing the springs, initiating the injection and retraction cycle.

Referring now to FIG. 13A to 13G, a further alternate fluid dispensing device 800 is held against the skin of the living organism 14 in any manner, such as by a self-adhesive surface 801, to the adhesive surface of which is revealed by removal of a strip 803. The device 800 is activated by pulling out a release tab 802. As a safety feature, there is a small snap fit 804 on the release tab 802. The retention forces exerted by this snap fit 804 must be overcome before it can be removed from the device 800. Once the release tab 802 is removed, a compression spring 806 drives a slider 810 forward. A cam surface 812 on the slider 810 provides a cam action on a needle holder 814 causing the needle holder 814, and the needle 816 affixed thereto, to depress in the vertical direction. The needle 816 has a first end 820 adapted to pierce a reservoir septum 822 in a flexible membrane 824 and a second end 826 adapted to pierce the skin of a living organism 14. A certain amount of travel, on the order of 2 mm, is permitted so that the needle 816 may penetrate to a desired depth in the skin of the living organism 14. This motion inserts the second end 826 of the needle 816 into the skin and the other end into the reservoir septum 822. As the motion continues, the reservoir 824 is compressed by the slider acting on the needle holder 814, forcing the fluid stored in the reservoir 824 through the needle 816 and into the living organism 14. Once the slider 810 reaches the end of its travel, it clears the needle holder 814. Consequently, the needle holder 814 and thus the needle 816 are free to return to its nominal state which retracts the needle from the skin. The reservoir 824 may optionally have a septum stop in which the first end of the needle plunges, which plugs the needle thereby preventing aspiration of the fluid of the living organism upon retraction of the needle.

Referring to FIG. 14A to FIG. 14H, an alternate fluid dispensing device 500 uses a torsion spring 537, mounted in a known manner between the housing 532 and a crank 533. When triggered, the torsion spring 537 turns the crank 533 which, via a rod 535 pivotally attached between the crank and a piston block 534, primes the needle 512 and plunges the same into the living organism 14 (or vice versa), dispensing fluid and then retracting the needle 512 out of the living organism safely into the housing. The needle 312 is affixed to a piston block 534 which is formed to slide in a channel in the housing 532, from a first position, in which the first end 314 of the needle 312 is adjacent a flexible hollow membrane 522 to a second position in which the fluid in the flexible hollow membrane has been squeezed out by the block through the needle 312 into the living organism 14.

Figure 14A:
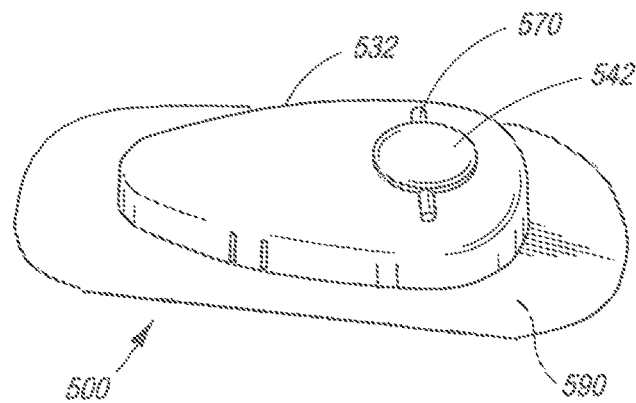
FIG. 14A is a perspective view of an eighth alternate embodiment of the invention.
Figure 14B:
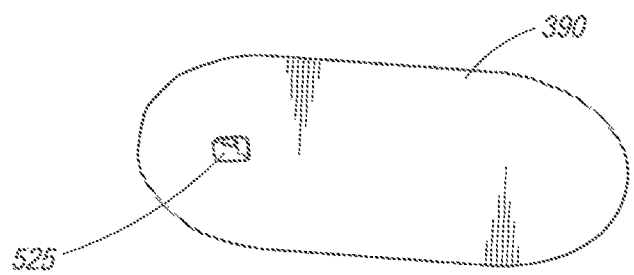
FIG. 14B is a second perspective view of the eighth alternate embodiment of the invention, from the underside.
Figure 14C:
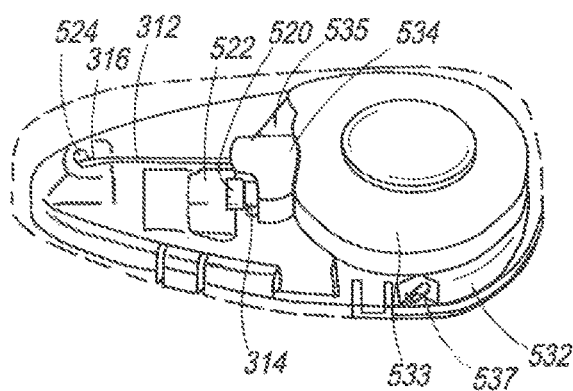
FIG. 14C is a perspective view of the eighth alternate embodiment of the invention in which a covering is transparent.
Figure 14D:
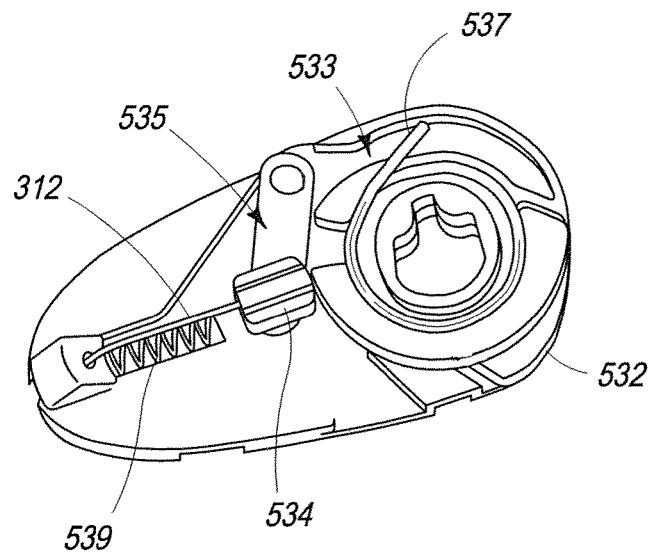
FIG. 14D is a perspective view of a progressive movement of the mechanism of the eighth alternate embodiment of the invention.
Figure 14E:
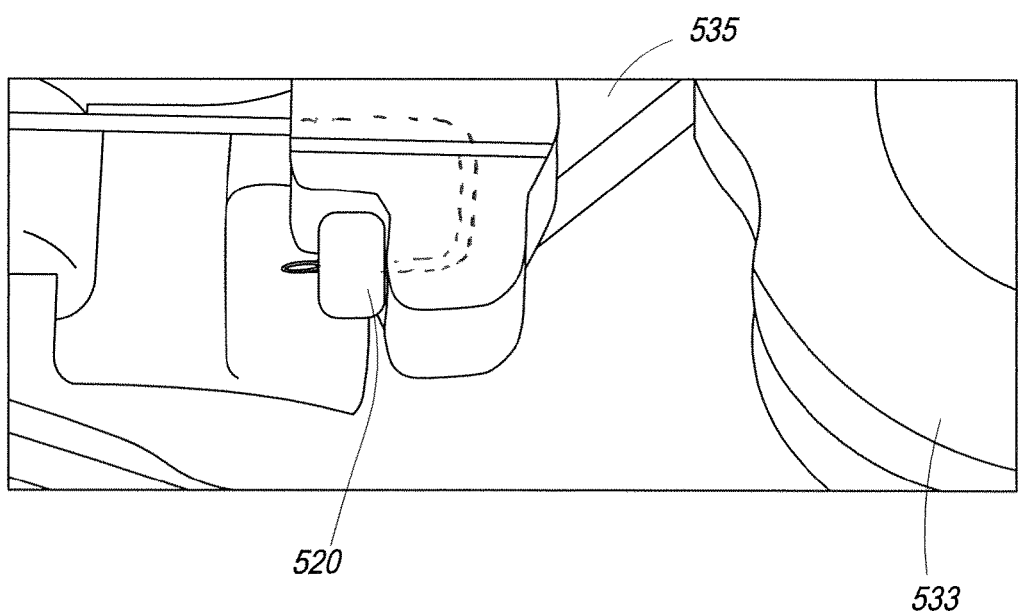
FIG. 14E is a perspective view of a further progressive movement of the mechanism of the eighth alternate embodiment of the invention.
Figure 14F:
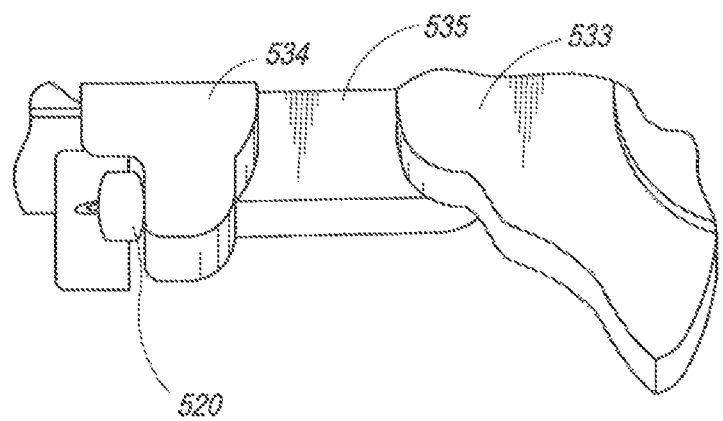
FIG. 14F is a perspective view of a further progressive movement of the mechanism of the eighth alternate embodiment of the invention.
Figure 14G:
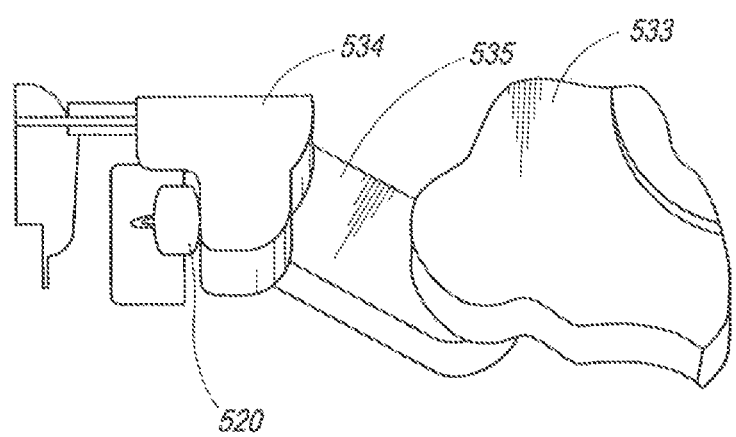
FIG. 14G is a perspective view of a progressive movement of the mechanism of the eighth alternate embodiment of the invention.
Figure 14H:
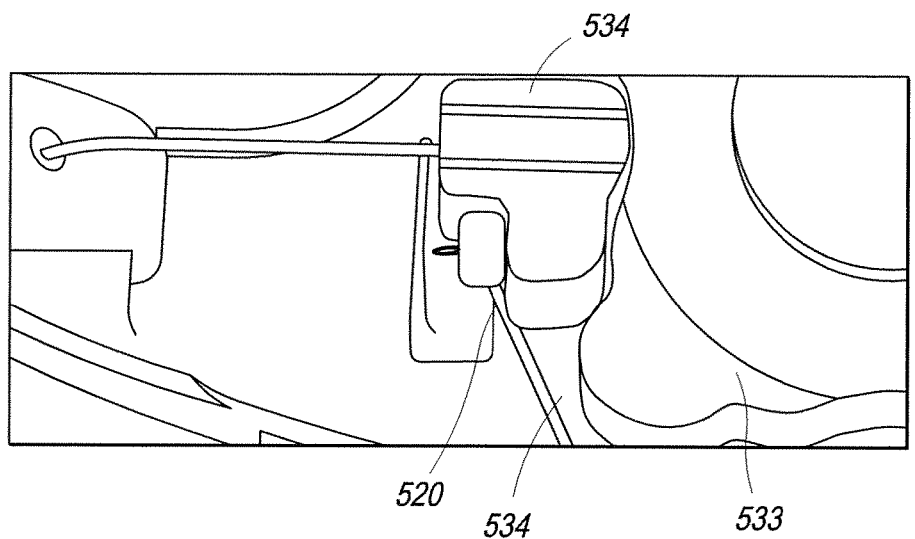
FIG. 14H is a perspective view of a further progressive movement of the mechanism of the eighth alternate embodiment of the invention.

Referring in particular to FIG. 14B, a hole 525 that allows the needle 312 to pass through the housing into the skin of the patient. In order to better sanitize the device, a thin membrane may cover this hole 525, thereby preventing a buildup of adhesive in the hole over several wearings of the device. The versions having an auto-adhesive protected by a removable layer or tab need not have such a thin membrane covering the hole 525 because the removable layer or tab fulfills this function.

In operation, a user removes a security pin 570 which releases a push button 542. The user then depresses the push button 542, which releases the crank 533. The rod 535, pivotally attached between the crank 533, translates the piston block 534 against the flexible membrane 522, plunging the first end 314 of the needle 312 into a septum 520 and, as motion continues, priming the needle and moving the second end 316 of the needle, guided by the guide 524, plunging into the living organism (or vice versa), dispensing the fluid therein, and then, as the crank rotates further, biased by return spring 539, drawing the needle out of the living organism 14 safely into the housing 532.

Figure 15:
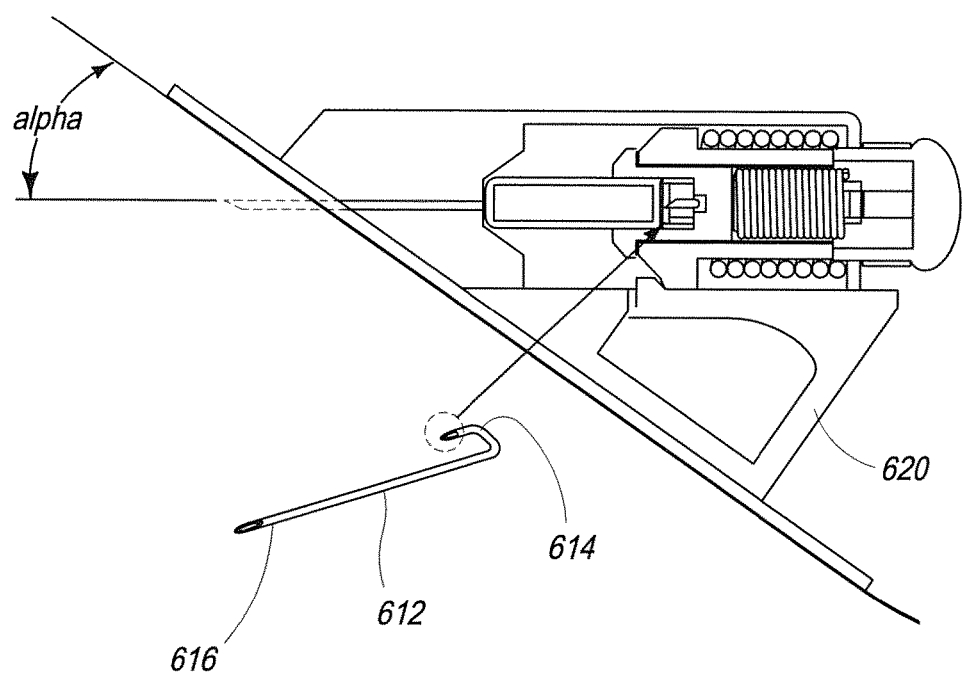
FIG. 15 is a cross sectional view of a ninth alternate embodiment of the invention, in which the mechanism is inclined with respect to the surface of the skin, allowing for a straight needle.

Referring now to FIG. 15, in an alternate exemplary embodiment, adaptable to the embodiments associated with FIGS. 10 to 14G, the needle 612 need not have the angled portion 316, but rather may extend out straight, parallel with the first end 614 which pierces the septum. The first and second end 614, 616, respectively, of the needle 612 pierce their respective piercing surface while translating together in a common direction. This is possible when the entire injection assembly, instead of being laid out parallel to the base plane, is laid out coplanar to the injection angle. The housings of the embodiments may be so adapted or the device may be mounted on an angled pedestal 620.

Figure 16A:
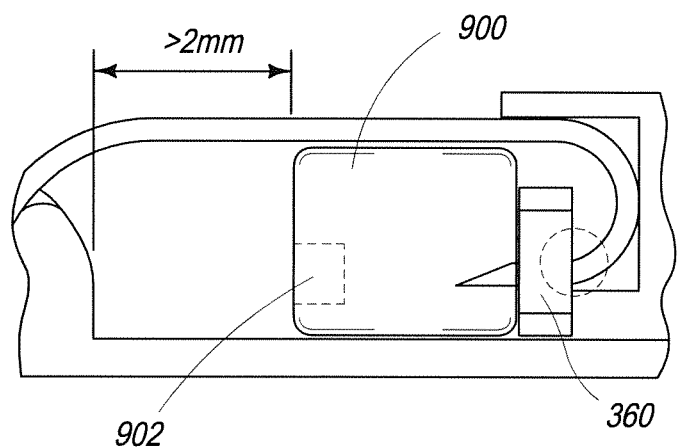
FIG. 16A is a schematic side view of an alternate embodiment of the fluid reservoir of the invention having a septum-like stop or plug.
Figure 16B:
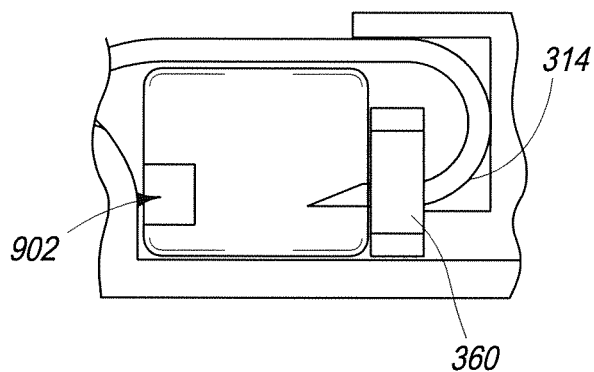
FIG. 16B is a further progression of the fluid reservoir of FIG. 16A during operation of the invention.
Figure 16C:
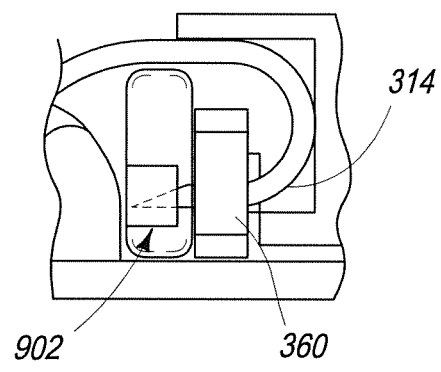
FIG. 16C is a further progression of the fluid reservoir of FIG. 16A during operation of the invention.

Referring now to FIGS. 16A to 16C, an alternate embodiment of the flexible fluid reservoir 900 is shown which prevents aspiration of the injected fluid upon removal of the needle. This functionality is important because in normal subcutaneous injection protocol, the needle is first inserted a certain depth under the skin (3 to 5 mm), and only after insertion, does one inject the drug under the epidermis. Finally, the needle is withdrawn. Unless such embodiment or its equivalent is used, the fluid will be distributed linearly throughout the penetration of the needle into the skin, from the surface until the final depth. Upon removal of the latter, there is a measurable risk that a portion of the injected fluid with be aspirated back into the needle. In the instant embodiment, the fluid reservoir 900 includes a septum-like stop 902 adjacent the bottom or far end (with respect to the first end of the needle) of the fluid reservoir 900, in which the first end 314 of the needle 312 will lodge upon completion of the injection cycle, thus blocking the first end of the needle completely and thereby preventing any unwanted re-aspiration of the injected fluid. Alternatively, instead of a septum-like stop or plug 902, a one way valve (not shown) or a reservoir that does not permit refilling may be used to prevent aspiration of fluids from the body back into the reservoir.

Figure 17:
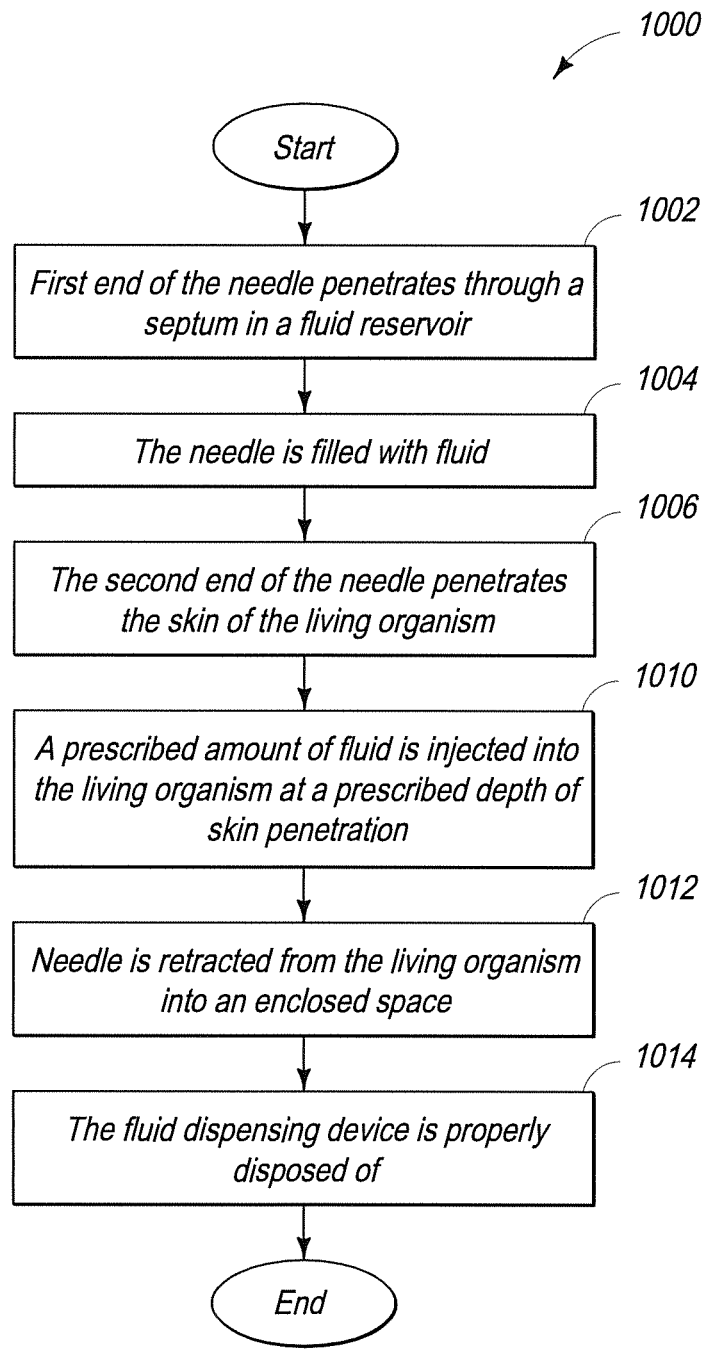
FIG. 17 is a flow chart of a method of the invention.

Referring to the septum 360, it is desirable to the function of the invention that the first end 314 of the needle 312 remains lodged therein during delivery and retraction. The septum is formed such that the force required to pull the distal end of the needle out of the septum must be greater than the forces required to retract the needle and for the reservoir body to slide back within the device. Alternatively, the septum-like stop 902 helps ensure that the reservoir remains fixed to the needle during retraction Referring to FIG. 17, in another aspect of the invention, a method 1000 is provided for subcutaneously administering a fluid to a living organism 14. The method 1000 includes the following steps. In a first step 1002, the first end 314 of the needle 312 penetrates through a septum 360 in a fluid reservoir 322. In a second step 1004, the needle 312 is filled with fluid. In a third step 1006, the second end 316 of the needle 312 penetrates the skin of the living organism 14. In a fourth step 1010, a prescribed amount of fluid is injected into the living organism 14 at a prescribed depth of skin penetration. In a fifth step 1012, the needle is retracted from the living organism 14 into an enclosed space. In a sixth optional step 1014, the fluid dispensing device is properly disposed of.

Figure 18:
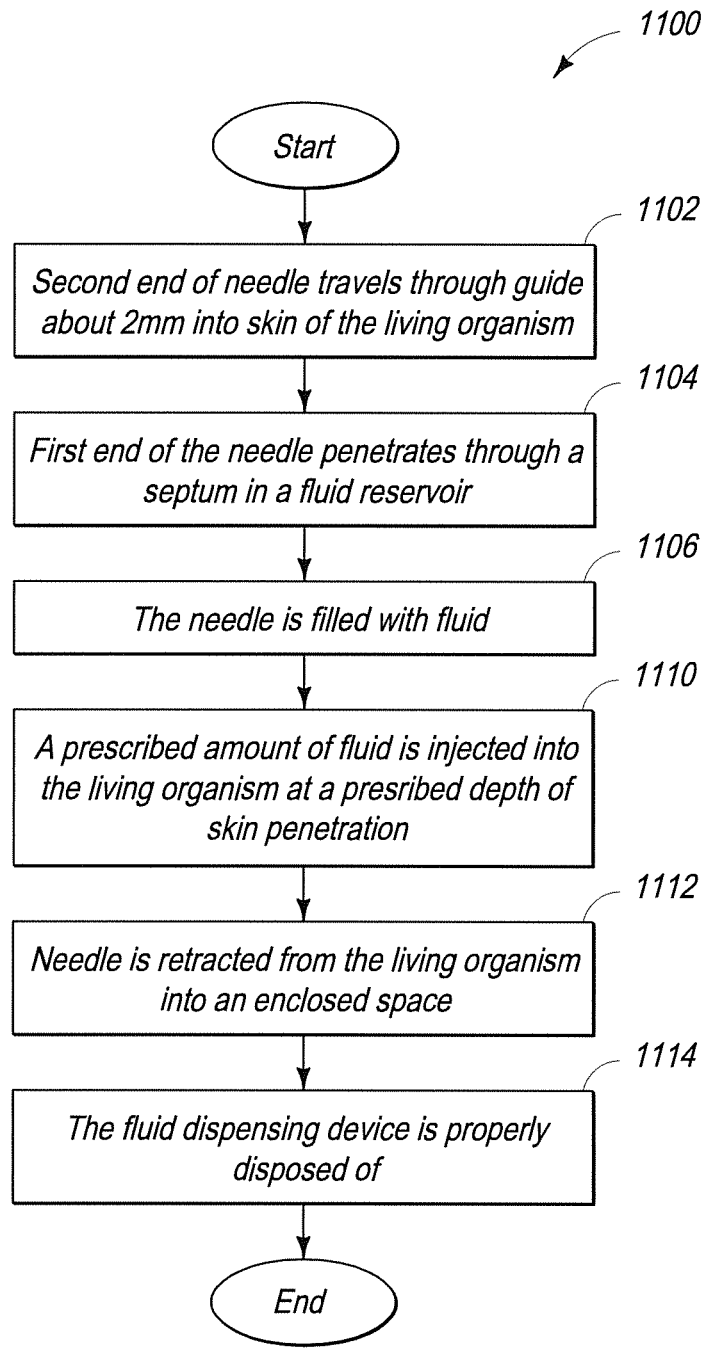
FIG. 18 is a flow chart of an alternate method of the invention.

Referring now to FIG. 18, in a further alternate method 1100 includes several steps. In a first step 1102, the second end 316 of needle 312 travels through a guide 324 about 2 mm into skin of the living organism. In a second step 1104, the first end 314 of the needle 312 penetrates through a septum 360 in a fluid reservoir 322. In a third step 1106, the needle 312 is filled with fluid. In a fourth step 1110, a prescribed amount of fluid is injected into the living organism 14 at a prescribed depth of skin penetration. Here, optionally, the first end of the needle penetrates into a septum-like stop or plug, as shown in FIGS. 16A to 16C. In a fifth step 1112, the needle 312 is retracted from the living organism 14 into an enclosed space. In a sixth step 1114, the fluid dispensing device is properly disposed of.

Figure 19A:
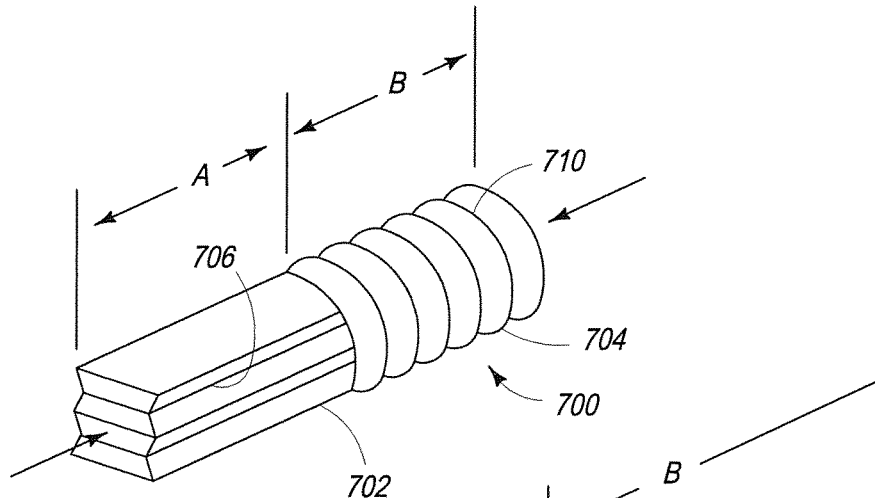
FIG. 19A is a perspective view of a first embodiment of the membrane of the invention.
Figure 19B:
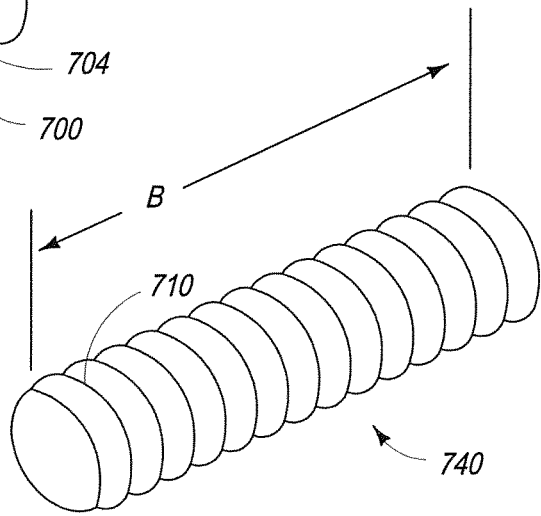
FIG. 19B is a perspective view of a second embodiment of the membrane of the invention.
Figure 19C:
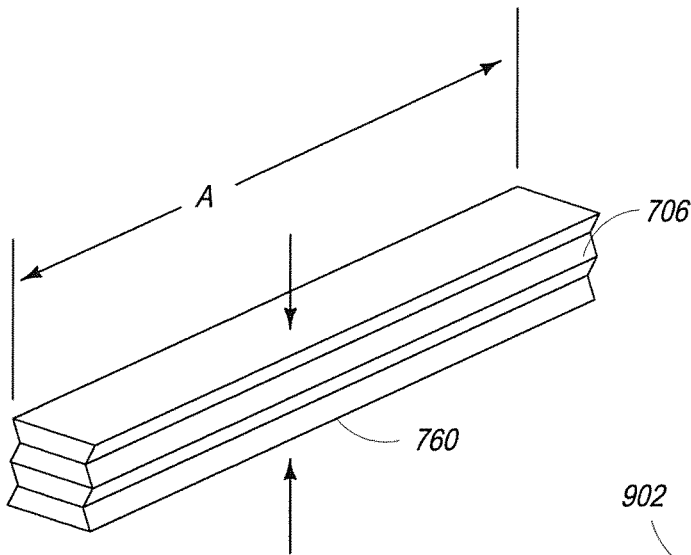
FIG. 19C is a perspective view of a third embodiment of the membrane of the invention.

Referring now to FIG. 19A to 19D, the flexible fluid membrane to be used with the invention may take on an almost infinite variety of forms. Referring now to FIG. 19A, by way of example, a flexible fluid membrane 700 particularly suitable for the embodiments described in FIGS. 11A to 11G has a first accordion portion 702 and a second accordion portion 704 joined together to form a single elongated membrane. The accordion portion 702 has a length A and is formed to have accordion folds 706 which permit collapsing of the portion 702 when squeezed laterally, by, for example, the receiver 340. The portion 704, on the other hand, has accordion folds 710 which are collapsible in the axial direction. Further, because the membrane 700 has a form having two portions each of which being compressible in a different direction, and the membrane is adaptable to vary the amount of fluid injected during the injection process. For example, the diameter or size of each portion 702 or 704 can be varied, and where each is activated in series, such as by the embodiment of FIGS. 11A to 11G, two injection rates may be selected, the first as the portion B compresses and the second rate associated with the lateral squeezing of the portion A. Referring in particular to FIGS. 19B to 19C, only one portion 702 or 704 may be used as well. With respect to the embodiment shown in FIG. 19C, this is most appropriate where there is no appreciable axial squeezing (see FIG. 11A) and only a pinching at the end of motion of the collet 340.

Figure 19D:
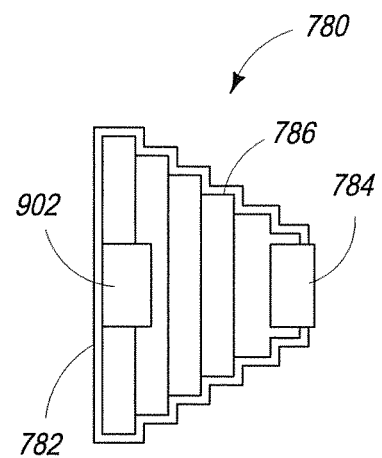
FIG. 19D is a cross-sectional view of a fourth embodiment of the membrane of the invention.

Referring now to FIG. 19D, a membrane 780 which is typical for use with the embodiments shown in FIGS. 12A-14H is either square or circular in lateral cross section, and pyramidal in axial cross section, in which the larger surface 782 is distal to the first end 314 of the needle 312 when this end is inserted into a septum 784, at its proximal end. A septum-like stop 902 is affixed to this larger surface 782, such that the first end 314 of the needle 312 will become lodged therein, blocking the needle and thereby preventing aspiration. Accordion folds 786 enable displacement of most of the fluid contained in the reservoir 780, by allowing an orderly collapsing of the membrane to a flat condition. The lodging of the first end 314 of the needle 312 into the stop also ensures that the membrane 780 does not expand (and so does not aspirate) because the first end 314 essentially locks the membrane from one septum 784 to the stop 902 against further expansion.

The membranes are inserted in the infusion device 400 pre-filled upon assembly of the device in a sterile environment, at the manufacturer's facility. As these devices 400 are intended for single use only, the user or doctor are not intended to have any interaction with the device, other than to attach the device, trigger and remove the device. This ensures that the device is single use only.

Figure 20A:
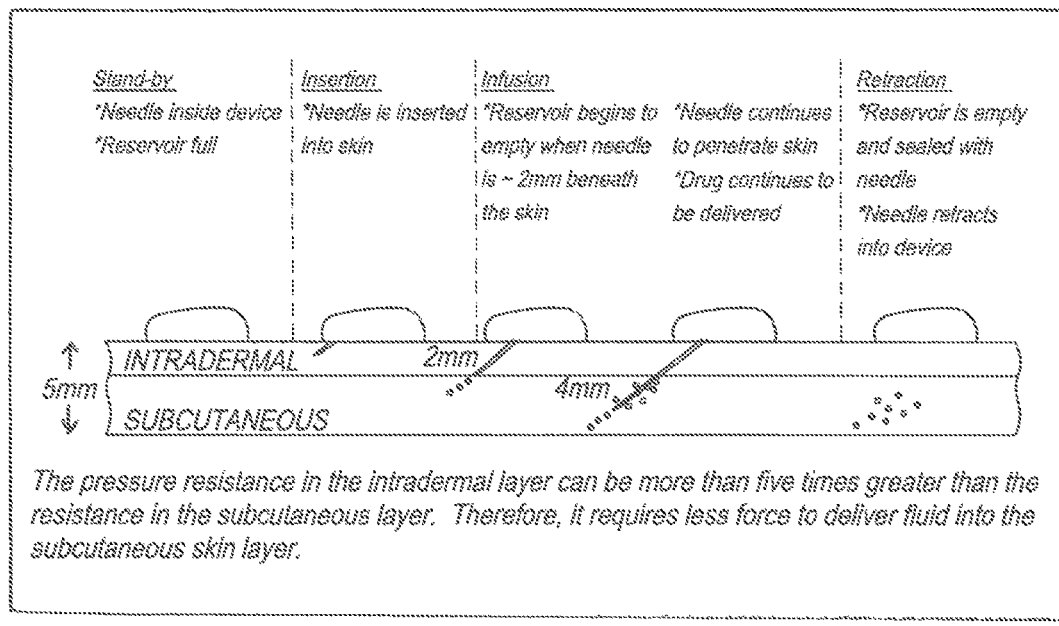
FIG. 20A is a schematic representation of the injection process of the invention.
Figure 20B:
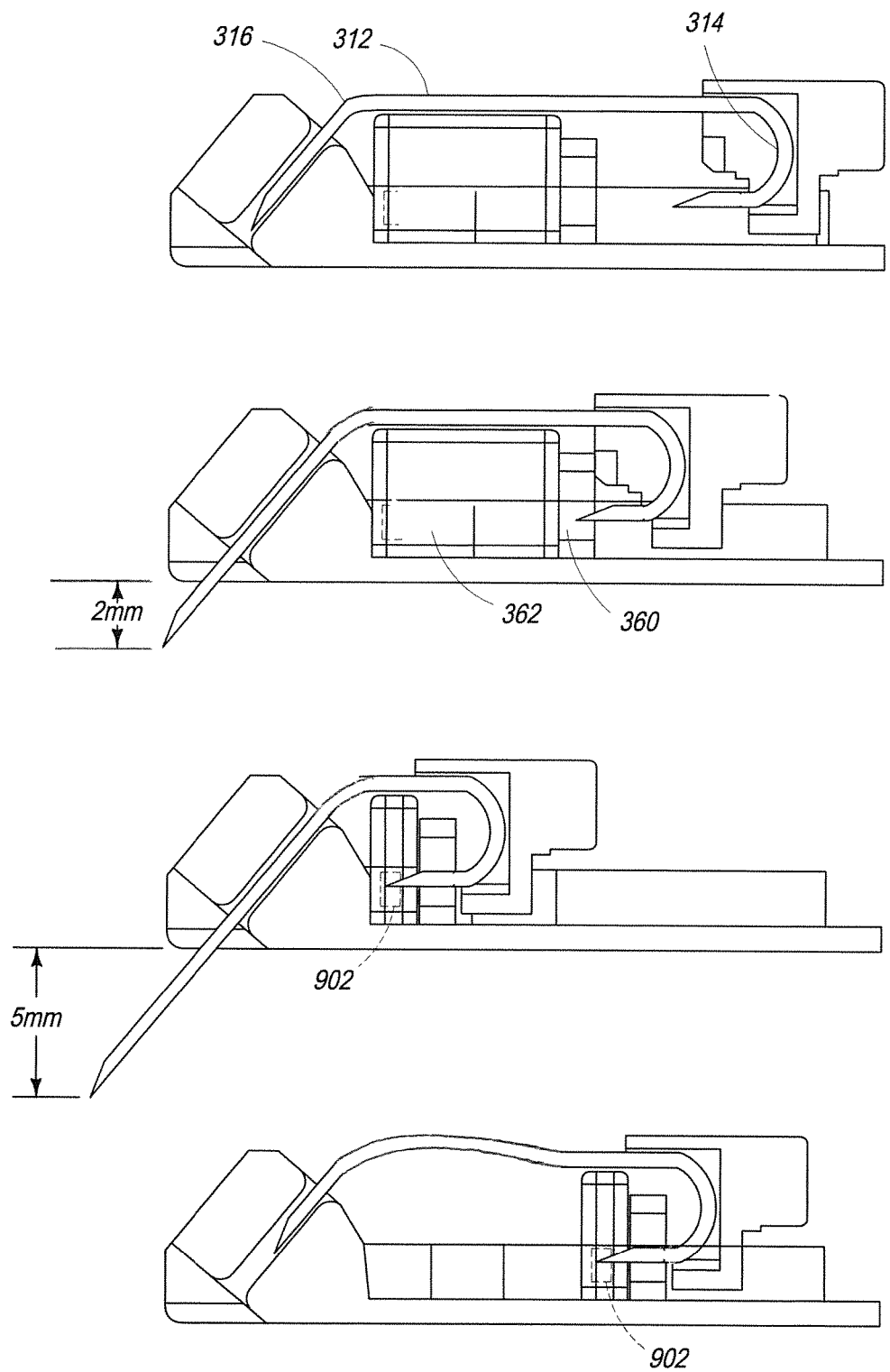
FIG. 20B is a schematic progression of an injection performed using the invention showing needle deformation during injection and retraction.

Referring now to FIG. 20, a progression of an injection performed using the invention includes a standby, an insertion, an infusion and a retraction stage. In the standby stage, the needle is inside the device and the fluid reservoir is full, with the device held against the skin of the patient. In the insertion stage, the needle is inserted 1.5 mm to 2 mm beneath the skin into the intradermal skin layer. In the infusion stage, the fluidic channel is then opened and the reservoir begins to empty as the needle continues to travel to the 4 mm to 5 mm subcutaneous target depth. The needle is fixed within the reservoir septum and as it retracts, the reservoir/septum slide with it. The flow rate depends greatly on the reservoir design (material properties, geometry, etc), size of the fluidic channel (needle inner diameter), and resistance beneath the skin. Once the reservoir begins to empty through a 27-31G (ultra-fine) needle 312, enough resistance is present to slow the spring travel so that the first bolus is thus delivered before the needle is retracted from the skin.

Optionally, an indicator indicates whether the injection has been completed. It is important to provide feedback so the user knows the infusion process is complete and the device is ready for removal. Alternatively, a snap type interface can be implemented, so as the spring retracts, there is a "click" when the needle holder reaches the final position. A viewing window can be implemented as well, where a portion of the needle is flagged with a color, this portion moving behind a window, indicating that the needle holder has retracted.

Optionally, an adhesive may be applied to the base for retaining the dispensing device against a wearer's skin. In one embodiment, the adhesive is an adhesive pad fixedly attached to the base and having a protective sheet on an opposite face thereof which allows removal to expose the adhesive surface.

The flexible hollow membrane has a fluid (e.g., any fluid including those listed above) therein and is functionally disposed in the receiver.

In an embodiment, the trigger mechanism is controlled by a sensor or a wireless radio receiver by remote control. The control of speed of the injection may be made as a function of time by, for example, controlling a micro motor actuator which replaces in these embodiments, the function of the compression spring 338, 438, 806, 537. Such motor (e.g. Squiggle) can be made such that it is part of a modular component which may be removably inserted into the device and removed for reuse, thus allowing the device to be made inexpensively, while permitting a more expensive actuation and control system. Such device may be illustrated by the unit of FIG. 10 in which the motor and electronics are integrated in the upper portion 200, while the dose and injection/retraction mechanism is located in the main housing 16'.

In another embodiment, the device includes a second housing for housing the trigger mechanism. The second housing is releasably connectable to the main housing.

It should be understood that both the invention can be used for extended bolus as well as by patients not capable of keeping the automatic injector steady against the injection site for the time required for conventional automatic injections (e.g., a few seconds).

In an advantage, the invention provides a low-profile automatic injector or infusion device which is less likely to be inadvertently torn off the wearer, when such device is adhered to or held against the skin of a living organism using a holding device.

In another advantage, the invention provides a reliable and simple means of injecting a living organism.

In another advantage, the invention provides for reliable self-injection.

In another advantage, the size of the device, as well as the fact that the mechanism is enclosed, render the device impossible to use a second time, thereby eliminating the risk of contamination of a second user or transmission of a disease of a first user to a second user.

In another advantage, the fluid dispenser is suitable for being left on the living organism many hours, even days, available in the event that such is needed.

In another advantage, a fluid dispenser is provided whose profile is not, as a minimum, the depth of penetration of the needle used in the injection.

In another advantage, because the amount of active agent, drug or other fluid required to have its therapeutic effect is typically very small, preparations are currently typically highly diluted in order for the physician or nurse can see (via the scale on the needle reservoir circumference) the amount injected. Consequently, because the invention can inject the required amount of active ingredient for a typical treatment, the invention is adaptable to self-use and to sterile injections of essentially any therapeutic fluid for the treatment of many illnesses.

It should be appreciated that the particular implementations shown and described herein are representative of the invention and its best mode and are not intended to limit the scope of the present invention in any way. Furthermore, any connecting lines shown in the various figures contained herein are intended to represent exemplary functional relationships and/or physical couplings between various elements. It should be noted that many alternative or additional physical connections or functional relationships may be present and apparent to someone of ordinary skill in the field.

Moreover, the apparatus, system and/or method contemplate the use, sale and/or distribution of any goods, services or information having similar functionality described herein.

The specification and figures are to be considered in an illustrative manner, rather than a restrictive one and all modifications described herein are intended to be included within the scope of the invention claimed, even if such is not specifically claimed at the filing of the application. Accordingly, the scope of the invention should be determined by the claims appended hereto or later amended or added, and their legal equivalents rather than by merely the examples described above. For instance, steps recited in any method or process claims should be construed as being executable in any order and are not limited to the specific order presented in any claim. Further, the elements and/or components recited in any apparatus claims may be assembled or otherwise operationally configured in a variety of permutations to produce substantially the same result as the present invention. Consequently, the invention is not limited to the specific configuration recited in the claims.

Benefits, other advantages and solutions mentioned herein are not to be construed as necessary, critical, or essential features or components of any or all the claims.

As used herein, the terms "comprises", "comprising", or any variation thereof, are intended to refer to a non-exclusive listing of elements, such that any process, method, article, composition or apparatus of the invention that comprises a list of elements does not include only those elements recited, but may also include other elements described in this specification. The use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or otherwise adapted by the skilled artisan to other design without departing from the general principles of the invention.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures which may be considered new, inventive and industrially applicable.

Multiple variations and modifications are possible in the embodiments of the invention described here. Although certain illustrative embodiments of the invention have been shown and described here, a wide range of modifications, changes, and substitutions is contemplated in the foregoing disclosure. While the above description contains many specifics, these should not be construed as limitations on the scope of the invention, but rather as exemplifications of one or another preferred embodiment thereof. In some instances, some features of the present invention may be employed without a corresponding use of the other features. In addition, the term "flexible" as used herein encompasses the concept of variable, in that a variable volume reservoir should be considered a flexible chamber, even if no individual components flex. Accordingly, it is appropriate that the foregoing description be construed broadly and understood as being given by way of illustration and example only, the spirit and scope of the invention being limited only by the claims which ultimately issue in this application.

What is claimed is:

1. A fluid dispensing device for dispensing a measured amount of fluid in a membrane into a living organism, the device having a needle having a first proximal end and a second distal end and a septum-stop, the needle interfacing, on the first proximal end, with a septum, and at the second distal end thereof, the needle free to translate in a first direction during which translation the needle is deformed through a guide which bends the needle at its distal end as the needle translates through the guide and, when in its operational position, the needle is positioned for subcutaneous insertion, and wherein the first proximal end of the needle is lodged into the septum-stop after piercing the septum, thereby ensuring that the membrane does not expand and so does not aspirate, and wherein further the needle is malleable such that it deforms during injection so as to function only for a single use.

2. The dispensing device of claim 1, wherein the second end of the needle is guided by the guide to be bent to an insertion angle permitting an injection into the living organism at a substantially non-orthogonal angle with respect to a surface of the living organism.

3. The device of claim 1, wherein the device is adapted for dispensing a fluid selected from one of a group of fluids consisting of peptides, proteins, hormones including insulin, calcitonin, calcitonin gene regulating protein, atrial natriuretic protein, colony stimulating factor, betaseron, erythropoietin (EPO), interferons including .alpha., .beta. or .gamma. interferon, somatropin, somatotropin, somastostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins including interleukin-2, and analogues or antagonists thereof, including IL-1ra; analgesics including fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof; anti-migraine agents including sumatriptan, ergot alkaloids, and analogues thereof; anti-coagulant agents i including heparin, hirudin, and analogues thereof; anti-emetic agents including scopolamine, ondansetron, domperidone, metoclopramide, and analogues thereof; cardiovacular agents, anti-hypertensive agents and vasodilators including diltiazem, clonidine, nifedipine, verapamil, isosorbide-5-monotritate, organic nitrates, agents used in treatment of heart disorders, and analogues thereof; sedatives including benzodiazepines, phenothiazines, and analogues thereof; chelating agents including defroxanune, and analogues thereof; anti-diuretic agents including desmopressin, vasopressin, and analogues thereof; anti-anginal agents including fluorouracil, bleomycin, and analogues thereof; anti-neoplastics including fluorouracil, bleomycin, and analogues thereof; prostaglandins and analogues thereof; and chemotherapy agents including vincristine, and analogues thereof, treatments for attention deficit disorder, methylphenidate, fluvoxamine, bisoprolol, tacrolimus, sacrolimus and cyclosporin, vitamins suspended in a liquid carrier, antivenoms, syrums, medications, antibodies, tocilizumab, brentuximab vedotin, ofatumumab, bevacizumab, belimumab, certolizumab pegol, cetuximab, trastuzumab, adalimumab, canakinumab, ranibizumab, gemtuzumab ozogamicin, pertuzumab, denosumab, infliximab, golimumab, eculizumab, ustekinumab, natalizumab, panitumumab, denosumab, omalizumab, ipilimumab, and ibritumomab tiuxetan.

4. The device of claim 1, wherein the fluid dispensing device further has an indicator which indicates that the injection is complete.

5. A method of subcutaneously administering a fluid to a living organism, the method, using the fluid dispensing device of claim 1, including the steps of:
   a. with a first end of the needle, penetrating through a septum in a fluid reservoir;
   b. filling the needle;
   c. with the second end of the needle, penetrating the skin of the living organism;

d. injecting a prescribed amount of fluid into the living organism at a prescribed depth of skin penetration;

e. with the first end of the needle, plunging into a septum-stop while the second end of the needle continues to penetrate the skin of the living organism, the lodging of the first proximal end of the needle into the septum-stop thereby ensuring that the membrane does not expand and so does not aspirate, and wherein further the needle is malleable such that it deforms during injection so as to function only for a single-use;

f. retracting the needle from the living organism into an enclosed space; and g. optionally disposing of the fluid dispensing device.

6. A flexible fluid membrane adapted for use in the device of claim 1, the membrane including:

a. a first proximal end including the septum; and b. the second distal end including the septum-stop.

7. The membrane of claim 6, the membrane having a form selected to control the amount of fluid injected during the course of the injection process.

8. A method of subcutaneously administering a fluid to a living organism, the method, using the fluid dispensing device having a needle having a first proximal end and a second distal end and a septum-stop, the needle adapted for interfacing, on the first proximal end, with a septum, and at the second distal end thereof, for subcutaneously inserting into a living organism while translating in a first direction during which translation the needle is deformed through a guide which bends the needle at its distal end as the needle translates through the guide, the method including the steps of:

a. the second end of needle travels through the guide which deforms the needle as the needle travels at least 2 mm into skin of the living organism;

b. first end of the needle penetrates through a septum in a fluid reservoir;

c. the needle is filled with fluid;

d. a prescribed amount of fluid is injected into the living organism at a prescribed depth of skin penetration;

e. the needle further translates causing fluid flow to be blocked as the first end of the needle penetrates into the septum-stop;

f. the needle is retracted from the living organism into an enclosed space; and g. the fluid dispensing device is disposed of.

* * * * *